United States Patent
Hamamoto et al.

(10) Patent No.: US 8,927,209 B2
(45) Date of Patent: Jan. 6, 2015

(54) LIVER CANCER METHODS AND COMPOSITIONS

(75) Inventors: Yoshihiko Hamamoto, Ube (JP); Norio Iizuka, Ube (JP); Toshiaki Miura, Tokyo (JP); Toyoki Moribe, Tokyo (JP); Masaaki Oka, Ube (JP); Shigeru Tamatsukuri, Tokyo (JP)

(73) Assignee: Roche Molecular Systems, Inc., Pleasanton, CA (US)

( * ) Notice: Subject to any disclaimer, the term of this patent is extended or adjusted under 35 U.S.C. 154(b) by 689 days.

(21) Appl. No.: 12/528,982

(22) PCT Filed: Mar. 1, 2008

(86) PCT No.: PCT/EP2008/001640
§ 371 (c)(1),
(2), (4) Date: Aug. 27, 2009

(87) PCT Pub. No.: WO2008/107134
PCT Pub. Date: Sep. 12, 2008

(65) Prior Publication Data
US 2010/0304372 A1    Dec. 2, 2010

(30) Foreign Application Priority Data

Mar. 2, 2007 (JP) .................................. 2007-53312
Jan. 31, 2008 (JP) ............................... 2008-021438

(51) Int. Cl.
C12Q 1/68 (2006.01)
C12P 19/34 (2006.01)
C07H 21/02 (2006.01)
C07H 21/04 (2006.01)

(52) U.S. Cl.
CPC ........ C12Q 1/6886 (2013.01); *C12Q 2600/118* (2013.01); *C12Q 2600/106* (2013.01); *C12Q 2600/112* (2013.01); *C12Q 2600/154* (2013.01)
USPC .......................... 435/6.1; 435/91.2; 536/24.3

(58) Field of Classification Search
CPC ........... C12Q 1/6886; C12Q 2600/112; C12Q 2600/118; C12Q 2600/154
See application file for complete search history.

(56) References Cited

U.S. PATENT DOCUMENTS

2007/0048738 A1    3/2007    Donkena et al.

FOREIGN PATENT DOCUMENTS

| EP | 1342794 A1 | 9/2003 |
|----|-----------|--------|
| EP | 1342794 B1 | 12/2005 |
| EP | 2008001640 | 9/2008 |
| WO | 2006002344 A1 | 1/2006 |
| WO | 2006128140 A2 | 11/2006 |

OTHER PUBLICATIONS

Rodriquez-Dorantes et al, Journal of Steroid Biochemistry and Molecular Biology, vol. 80, 2002, pp. 323-330.*

Kobunai et al; Proc Amer Assoc Cancer Res, vol. 47, 2006, abstract #37(2 pages).*

Carpenter, Brian, et al., 2004, "BASP1 Is a Transcriptional Cosuppressor for the Wilms' Tumor Suppressor Protein WT1", Molecular and Cellular Biology, 24(2):537-549.

Fitzgibbon, M. J., et al., 2000, "Assignment of brain acid-soluble protein1 (BASP1) to human chromosome 5p15.1—p14, differential expression in human cancer cell lines as a result of alterations in gene dosage" Cytogenetics and Cell Genetics, 89:147-149.

Fleischhacker, M. and Schmidt, B., 2007, "Circulating Nucleic Acids (CNAs) and cancer—A survey", Biochimica et Biophysica Acta, 1775:181-232.

Fukai, Kenichi, et al., 2003, "Hepatocyte Growth Factor Activator Inhibitor 2/Placental Bikunin (HAI-2/PB) Gene is Frequently Hypermethylated in Human Hepatocellular Carcinoma", Digestive Disease Week Abstracts and Itinerary Planner, 2003:T1756: XP002485660; & Digestive Disease 2003; Orlando, Florida, USA, May 17-22, 2003, 8675(2)-8677(2:1).

Fukai, Kenichi, et al., 2003, "Hepatocyte Growth Factor Activator Inhibitor 2/Placental Bikunin (HAI-2/PB) Gene is Frequently Hypermethylated in Human Hepatocellular Caricnoma", Cancer Research 63:8674-8679.

Iizuka, Norio, et al., 2006, "Elevated Levels of Circulating Cell-Free DNA in the Blood of Patients with Hepatitis C Virus-associated Hepatocellular Carcinoma", Anticancer Research, 26:4713-4720.

Lam, Tai-Wai, et al., 2006, "Correlative Analysis of DNA Methyltransferase Expression and Promoter Hypermethylation of Tumor Suppressor Genes in Hepatocellular Carcinoma", Cancer Genomics & Proteomics, 3:271-278.

Mosevitsky, M.I., et al., 1997, "The BASP1 Family of Myristoylated Proteins Abundant in Axonal Termini. Primary Structure Analysis and Physico-Chemical Properties", Biochimie, 79:373-384.

Rodriguez-Dorantes, M., et al., 2002, "Evidence that steroid 5alpha-reductase isozyme genes are differentially methylated in human lymphocytes", Journal of Steroid Biochemistry & Molecular Biology 80:323-330.

Roncalli, Massimo, et al., 2002, "Methylation Framework of Cell Cycle Gene Inhibitors in Cirrhosis and Associated Hepatocellular Carcinoma", Hepatology, 36(2):427-432.

(Continued)

*Primary Examiner* — Jehanne Sitton
(74) *Attorney, Agent, or Firm* — Olga Kay

(57) ABSTRACT

The present invention provides a novel method for detection of liver cancer. This method detects high-sensitively, high-specifically, simply and accurately liver cancer, especially that in early stage by identifying and/or quantifying methylation on particular genes and/or their DNA fragments in clinical specimens, and by combining said methylated DNA values with existing tumor marker values and/or DNA amounts in blood. This invention also detects a precancerous lesion, detects a risk of recurrence after treatment of liver cancer, detects malignancy of liver cancer and monitors progression of liver cancer with time by the same method. As for particular genes, BASP1 gene, SPINT2 gene, APC gene, CCND2 gene, CFTR gene, RASSF1 gene and SRD5A2 gene are mentioned.

14 Claims, 5 Drawing Sheets

(56) References Cited

OTHER PUBLICATIONS

Rossi, L., et al., 2003, "Genetic Polymorphisms of Steroid Hormone Metabolising Enzymes and Risk of Liver Disease Progression and Cancer in Hepatitis C Infected Patients", Journal of Hepatology, 38(2):17, XP002496941; & 38th Annual Meeting of the European Association for the Study of the Liver, Istanbul, Turkey, Mar. 29-Apr. 1, 2003, ISSN:0168-8278.

Usadel, Henning, et al., 2002, "Quantitative Adenomatous Polyposis Coli Promoter Methylation Analysis in Tumor Tissue, Serum, and Plasma DNA of Patients with Lung Cancer", Cancer Research, 62:371-375.

Yang, Bin, et al., 2003, "Aberrant Promoter Methylation Profiles of Tumor Suppressor Genes in Hepatocellular Carcinoma", American Journal of Pathology, 163(3):1101-1107.

Zhang, Changsong, et al., 2007, "CpG Island Methylator Phenotype Association with Elevated Serum alpha-Fetoprotein Level in Hepatocellular Carcinoma", Clinical Cancer Research, 13(3):944-952.

Zhu, Jingde, 2006, "DNA methylation and hepatocellular carcinoma", Journal of Hepatobiliary Pancreatic Surgery, 13:265-273.

GenBank Acc. No. NM_006317.3 (2006).

* cited by examiner

LIVER CANCER METHODS AND COMPOSITIONS

This application is a national stage of the PCT application PCT/EP2008/001640, which claims priority to JP Application 2008-021438 filed Jan. 31,2008; and to JP Application 2007-53312 filed Mar. 2,2007.

FIELD OF THE INVENTION

The present invention provides a method, a kit and a reagent to detect liver cancer, risk of liver cancer, risk of recurrence of liver cancer and malignancy of liver cancer, and to monitor progression with time of liver cancer by identifying and/or quantifying methylation on particular genes and/or their DNA fragments in clinical specimens.

BACKGROUND OF THE INVENTION

Liver cancer develops from chronic liver diseases (chronic hepatitis and liver cirrhosis), and most cases from those with persistent infection of hepatitis virus. In Japan over 95% of liver cancer patients have sustained infection with hepatitis B virus (HBV) and hepatitis C virus (HCV), especially over 80% of those derives from HCV-associates diseases. Generally, patients with hepatitis become more severe in phases in 20-30 years after hepatitis occurrence, and develop liver cancer after progression to liver cirrhosis. Especially, pre-liver cirrhosis phase (fibrosis degree F3) and liver cirrhosis (fibrosis degree F4) are associated with high rates of liver cancer, and it's said that those patients will develop liver cancer within 10 years.

The age of onset is 60 years and over, and more cases in old generations. There are cases to develop in relatively early stage and in lower generations after hepatitis occurrence. But the cause is as yet not well known. In the past, screening using immunological assay of existing tumor markers, AFP (alpha-fetoprotein) and PIVKA-II (protein induced by Vitamin K absence-II), and monitoring by an echo test (ultrasonography) for high risk patients of liver cancer have been regularly performed to detect liver cancer.

For patients who have been suspected to have liver cancer by those testing, the place, size and number of liver cancer are confirmed by diagnostic imaging, more detailed echo, CT (Computed Tomography) or MRI (Magnetic Resonance Imaging) tests. Furthermore liver cancer is finally diagnosed definitely using a pathological test by biopsy, if needed. Liver cancer which has been diagnosed definitely is undergone treatment; hepatectomy, transcatheter arterial embolization (TAE), puncture treatment (percutaneous ethanol injection therapy (PEIT), radiofrequency ablation (RFA) and microwave coagulation therapy (MCT)). However, recurrence rate of liver cancer is extremely high, as virus has been not removed and liver diseases have not been cured even if be treated.

If liver cancer is detected in early stage (below 3 cm in diameter, below 5 cm in diameter and a single or well-differentiated tumors) by the current immunological assay and echo test, and is treated properly, prognosis is relatively good. However, the sensitivity and specificity by existing tumor markers, AFP and PIVKA-II, which are employed for immunological assay, are insufficient. Especially, for liver cancer in early stage both markers have remarkably low sensitivities (see nonpatent literature 1, 2, 3 and 4). Therefore, it is difficult to detect liver cancer in early stage, most cases have already progressed to advanced cancer when detected, and the 5-year survival relative rate of liver cancer patients is very bad in comparison with other cancers (see nonpatent literature 5).

Meanwhile, recent improvement of instruments in an echo test has enabled us to detect liver cancer in early stage, but it is not suited to screening for high risk patients of liver cancer because of some troubles to take around 30 min for a test, to demand technical skills, to depend on performances of instruments and to remain low penetration rate over general hospitals. Furthermore, as it is difficult to examine whole liver, especially parts hidden by other organs and inside of liver completely, there is the risk overlook liver cancer. Thus, there have been no sufficiently satisfactory existing methods for detection of liver cancer, especially that in early stage.

Recent development of molecular biological technology is clarifying characteristics of DNA modification without any genetic changes and any alternations of nucleotide sequences in human cancer cells. Characteristics of changes, mutation, amplification and loss of genes, are well known as representative examples. By recent epigenetical study, there have been reports that particular genes are highly and abnormally methylated in variable cells, especially cancer cells.

In higher eukaryotes, genomic DNA is methylated at only cytosine residues in CpG dinucleotides, the CpG rich region is called as "CpG island" and it is known to exist on around half of whole human genome. Generally, the CpG island inhabits the promoter region, and in that case methylation is strongly concerned in regulation of gene expression. Briefly, in unmethylated cases genes are expressed (mRNA is transcribed), but in methylated cases gene expression is contrarily suppressed through some processes for regulation system. It is known that this regulation of gene expression by methylation is specific to tissue, development, differentiation, disease, sex or aging. Especially, as suppression of gene expression by abnormal high methylation on CpG island is frequently observed in cancer cells or transformed cells, it is considered to be related to carcinogenesis.

Based on those evidences in fundamental study, until now clinical studies with regard to association between abnormal high methylation on CpG island and carcinogenesis have been performed in variable cancers. In liver cancer similar clinical studies have been carried out, and it has been reported that abnormal high methylation on particular genes is observed in tumor tissues of liver cancer patients (see nonpatent literature 6, 7, and 8).

Accordingly, it is inferred that utilization of identification of methylation on particular genes in cancer cells or their DNA fragments for diagnosis is very useful for detection of cancer in early stage. Furthermore, methylation which is considered as one of factors directly relating to carcinogenesis is supposed to develop before cancer occurrence, to alter with progression or malignant alteration of cancer, and to show different profiles from differing patients or clinical conditions. Therefore, Identification of methylation has possibilities to enable to utilize for detection of precancerous lesion, prediction of recurrence after treatment of liver cancer, detection of malignancy of liver cancer and monitoring of progression of liver cancer with time.

However, the previous results of clinical studies are obtained using tumor tissue DNA after confirmed diagnosis for specimens to analyze, and can not meet a screening use for detection of liver cancer in early stage or risk of liver cancer occurrence. An assay using tissue is not suited to a routine testing due to complicated manipulation and very low capacity of sample processing. Furthermore, the sensitivity and specificity are insufficient because of improper selection of genes to analyze and a single gene usage for analysis. Thus, it has been very difficult to utilize identification of methylation on DNA fragments for cancer diagnosis practically.

Meanwhile, minute DNA is circulating in blood, and especially it is known that DNA amount in blood are rising in cancer patients (see nonpatent literature 9 and 10). It is considered to be led by which older cells are destroyed by program death (apoptosis) or necrosis and large quantities of DNA are released from them into blood, while tumor tissue continues to proliferate at abnormal speed. Because DNAs from variable tissues or blood cells as well as DNA which is derived from tumor tissue are included in blood, it has been difficult to discriminate DNA derived from a particular tumor tissue by using conventional technologies. But, to utilize DNA in blood for cancer diagnosis is very promising for practical application of diagnosis.

REFERENCES

[Patent literature 1] Tetzner R et al., WO 2004/113567:24-25, 2004
[Nonpatent literature 1] Nomura F et al. Am J Gastroenterol 94:650-4, 1999
[Nonpatent literature 2] Martinez Cerezo F J et al. Rev Esp Enferm Dig 84:311-4, 1993
[Nonpatent literature 3] He Y M et al. Hepatobiliary Pancreat Dis Int 4:50-4, 2005
[Nonpatent literature 4] Han S L et al. Hepatogastroenterology 52:348-51 2005
[Nonpatent literature 5] Osaka Cancer Registry, Annual report 2006
[Nonpatent literature 6] Yu J et al. Cell Res 13:319-33, 2003
[Nonpatent literature 7] Kanai Y et al. Hepatology 29:703-9, 1999
[Nonpatent literature 8] Kondo Y et al. Hepatology 32:970-9, 2000
[Nonpatent literature 9] Leon S A et al. J Immunol Methods 9:157-64, 1975
[Nonpatent literature 10] Ren N et al. World J Gastroenterol 12:3911-4, 2006
[Nonpatent literature 11] Herman J G et al., Proc Natl Acad Sci USA 93:9821-6, 1996.
[Nonpatent literature 12] Cottrell S E et al., Nucleic Acids Res 32:e10, 2004.
[Nonpatent literature 13] Eads C A et al., Nucleic Acids Res 28:e32, 2000.
[Nonpatent literature 14] Iizuka N et al., Lancet 361:923-929, 2003
[Nonpatent literature 15] The General Rules for the Clinical and Pathologic Study of Primary Liver Cancer Liver Cancer Study Group of Japan 2th ed. Tokyo: Kanehara&CO., LTD, 2003.

SUMMARY OF THE INVENTION

The purpose of this invention is to solve problems in screening or monitoring of liver cancer by an immunological assay with conventional tumor markers and an echo test for high risk patients of liver cancer, to discover new tumor markers detectable high-sensitively and high-specifically, even liver cancer in early stage which is difficult to detect by conventional methods, and to provide a simple, accurate and high-throughput method using those markers, and a kit and a reagent thereof. This invention also aims to present a method for liver cancer detection which can easily automate by using blood specimens as measuring targets. Furthermore, utilizing appropriate novel tumor markers, it's also an object of the invention to make a real possibility detection of precancerous lesion and prediction of recurrence after treatment of liver cancer for high risk patients of liver cancer, and detection of malignancy of liver cancer and monitoring of progression of liver cancer with time for liver cancer patients.

The inventors have, consequently, found out that it is surprisingly possible to detect liver cancer, especially that in early stage, high-sensitively, high-specifically, easily and accurately by identifying and/or quantifying methylation on two or more particular genes, or respective DNA fragments in clinical specimens, that it is possible to detect risk of liver cancer, risk of recurrence after treatment of liver cancer and malignancy of liver cancer easily, that it is possible to monitor progression of liver cancer with time easily, and have accomplished this invention.

Briefly, the main point of this invention is a method for detection of liver cancer, detection of risk of liver cancer, detection of recurrence after treatment of liver cancer, detection of malignancy of liver cancer and monitoring of progression of liver cancer with time. More specific, the invention is directed to the following processes:

A method for detecting the presence and/or amount of methylated cytosine specific to liver cancer on a region containing CpG sequences in BASP1 gene and/or SRD5A2 gene comprising steps (a) to (d) mentioned below, wherein the presence and/or amount of methylated cytosine specific to liver cancer in BASP1 gene and/or SRD5A2 gene in a sample from a patient is an indication that the patient is afflicted with cancer of the liver, has an increased risk of cancer of the liver, has a risk of recurrence after a treatment for cancer of the liver, has a malignant cancer of the liver or has a progressing cancer of the liver with time, the steps to be carried out are as follows:

(a) isolating the genomic DNA from the sample from the patient;
(b) providing a reagent for chemical or enzymatical treatments to the genomic DNA in order to discriminate between methylated and unmethylated cytosines;
(c) amplifying methylated cytosine-containing regions of BASP1 gene and/or SRD5A2 gene of the genomic DNA using PCR method; and
(d) determining the presence and/or amount of methylated cytosine specific to liver cancer on a region containing CpG sequences in BASP1 gene and/or SRD5A2 gene in the sample from the patient, which indicate that the patient is afflicted with cancer of the liver, has an increased risk of cancer of the liver, has a risk of recurrence after a treatment for cancer of the liver, has a malignant cancer of the liver or has a progressing cancer of the liver with time.

Another object of the invention is a method for indicating that a patient is afflicted with cancer of the liver, has an increased risk of cancer of the liver, has a risk of recurrence after a treatment for cancer of the liver, has a malignant cancer of the liver or has a progressing cancer of the liver with time by detecting the presence and/or amount of methylated cytosine specific to liver cancer on regions containing CpG sequences in at least two genes of BASP1 gene, SRD5A2 gene, SPINT2 gene, APC gene, CCND2 gene, CFTR gene or RASSF1 gene in the sample from the patient by the method comprising the following steps (a) to (d) and by using in combination with said presence and/or amount of methylated cytosine:

(a) isolating the genomic DNA from the sample from the patient;
(b) providing a reagent for chemical or enzymatical treatments to the genomic DNA in order to discriminate between methylated and unmethylated cytosines;

(c) amplifying methylated cytosine-containing regions of at least two genes of BASP1 gene, SRD5A2 gene, SPINT2 gene, APC gene, CCND2 gene, CFTR gene or RASSF1 gene of the genomic DNA using PCR method; and (d) determining the presence and/or amount of methylated cytosine specific to liver cancer on a region containing CpG sequences in at least two genes of BASP1 gene, SRD5A2 gene, SPINT2 gene, APC gene, CCND2 gene, CFTR gene or RASSF1 gene in the sample from the patient, which indicate that the patient is afflicted with cancer of the liver, has an increased risk of cancer of the liver, has a risk of recurrence after a treatment for cancer of the liver, has a malignant cancer of the liver or has a progressing cancer of the liver with time.

A more specified object of the instant invention is a method according to any of the processes mentioned above, wherein at least either nucleotide sequence of a pair of PCR primers is complementary to a nucleotide sequence in the genomic DNA on a region containing cytosine residues which can undergo methylation, and can specifically hybridize to said nucleotide sequence in the genomic DNA when said cytosines are methylated.

Alternatively, a preferred embodiment of the invention is a method according to the processes mentioned above, wherein at least either of a pair of PCR primers can specifically hybridize to a region containing no cytosine residues which can undergo methylation and oligonucleotides for blocking of amplification by said PCR primers are used simultaneously, which nucleotide sequences of said oligonucleotides partly overlap with nucleotide sequences of said PCR primers, are complementary to nucleotide sequences in the genomic DNA on a region containing cytosine residues which can undergo methylation at other parts and said oligonucleotides can specifically hybridize to said nucleotide sequences in the genomic DNA when said cytosines are not methylated.

A preferred embodiment of any of the processes described is, wherein a reagent for conversion of unmethylated cytosine to uracil is provided to the genomic DNA as a chemical treatment to the step (b), so that essentially all unmethylated cytosines of said DNA are converted to uracil. Preferably, the reagent for the conversion of unmethylated cytosine to uracil on said DNA is a bisulfite-containing reagent, e.g., sodium bisulfite and/or sodium sulfite and/or 6-hydroxy-2,5,7,8-tetramethylchroman-2-carboxylic acid.

Another preferred embodiment of any of the processes described is, wherein a restriction enzyme that is not able to digest recognition sites containing methylated cytosine and can digest recognition sites containing no methylated cytosine is provided to the genomic DNA as an enzymatical treatment to the step (b).

Preferred are blood samples, wherein concentration values of conventionally used tumor marker proteins, e.g., AFP and/or PIVKA-II, and/or free floating DNA amounts, e.g., amounts of GSTP1 gene, are simultaneously applied.

The methods according to the invention are preferred to determine liver cancer in early stages.

Samples to be used according to the instant invention are derived from human sera, plasma, whole blood, tissues, blood cells, excretions or internal/external secretion.

Furthermore, embodiments are preferred according to the invention, wherein a real-time PCR amplification using a fluorescent probe is performed to step (c).

The invention is also directed to a method, wherein a pair of PCR primers can specifically hybridize to nucleotide sequences in the genomic DNA containing no cytosine residues which can undergo methylation in at least its 3'-ends, and determination of the presence and/or amount of methylated cytosine in products which are amplified by said PCR primers are performed by sequencing analysis or by mass spectrometry to step (d).

The following primer pairs comprising two nucleic acid primers are preferred according to the invention:
1) BASP1_MSF (SEQ ID No.:1) and BASP1_MSR (SEQ ID No.:2)
2) SPINT2_MSF (SEQ ID No.:3) and SPINT2_MSR (SEQ ID No.:4)
3) APC_MSF (SEQ ID No.:5) and APC_MSR (SEQ ID No.:6)
4) CCND2_MSF (SEQ ID No.:7) and CCND2_MSR (SEQ ID No.:8)
5) CFTR_MSF (SEQ ID No.:9) and CFTR_MSR (SEQ ID No.:10)
6) RASSF1_MSF (SEQ ID No.:11) and RASSF1_MSR (SEQ ID No.:12)
7) SRD5A2_MSF (SEQ ID No.:13) and SRD5A2_MSR (SEQ ID No.:14)
8) BASP1_F (SEQ ID No.:15) and BASP1_R (SEQ ID No.:16)
9) PINT2_F (SEQ ID No.:17) and SPINT2_R (SEQ ID No.:18)
10) APC_F (SEQ ID No.:19) and APC_R (SEQ ID No.:20)
11) CCND2_F (SEQ ID No.:21) and CCND2_R (SEQ ID No.:22)
12) CFTR_F (SEQ ID No.:23) and CFTR_R (SEQ ID No.:24)
13) RASSF1_F (SEQ ID No.:25) and RASSFLR (SEQ ID No.:26)
14) SRD5A2_F (SEQ ID No.:27) and SRD5A2_R (SEQ ID No.:28)
15) SPINT2_HMF (SEQ ID No.:29) and SPINT2_HMR (SEQ ID No.:30).

The following probes preferred according to the invention are selected from a group consisting of:
1) BASP1_TMP (SEQ ID No.:31)
2) SPINT2_TMP (SEQ ID No.:32)
3) APC_TMP (SEQ ID No.:33)
4) CCND2_TMP (SEQ ID No.:34)
5) CFTR_TMP (SEQ ID No.:35)
6) RASSF1_TMP (SEQ ID No.:36)
7) SRD5A2_TMP (SEQ ID No.:37)
8) SPINT2_HMBF (SEQ ID No.:38)
9) SPINT2_HMBR (SEQ ID No.:39).

Another object of the invention is a kit, to be used for any of the methods for detecting the presence and/or amount of methylated cytosine base specific to a liver cancer or for indicating that a patient is afflicted with liver cancer or might be suffering from liver cancer in the future, said kit is comprising:
(a) at least one of the primer pairs specified above, and/or
(b) at least one of the probes specified above.

A further object of the invention is a reagent, to be used for any of the methods for detecting the presence or/and the amount of methylated cytosine base specific to liver cancer or for indicating that a patient is afflicted with liver cancer or might be suffering from liver cancer in the future, said reagent is comprising:
(a) at least one of the primer pairs specified above, and/or
(b) at least one of the probes specified above.

Another object of the invention is an instrument system, to be used for any of the methods described above comprising:
(a) at least one of the primer pairs specified above, and/or
(b) at least one of the probes specified above.

The invention is also directed to the use of a primer or a probe specified above for detecting the presence and/or amount of a methylated cytosine base specific to liver cancer on a region containing CpG sequences in a HCC related gene in a sample from a patient, or for detecting cancer of liver, an increased risk of cancer of the liver, a risk of recurrence after a treatment for cancer of the liver, a malignant cancer of the liver or a progressing cancer of the liver with time in a patient.

It is possible to detect liver cancer, especially that in early stage, in clinical specimens easily and accurately by the testing method in this invention, and it is expected to help improved outcome from treatment for liver cancer patients by detecting in advance a risk of liver cancer and a risk of recurrence after treatment of liver cancer. As another use, it is expected to provide an indication for decision of treatment course of liver cancer by detecting malignancy of liver cancer and monitoring progression of liver cancer with time.

DETAILED DESCRIPTION OF THE INVENTION (1) Liver Cancer Specific Methylation Genes The inventors selected genes whose expression level specifically reduced in tumor tissues, namely whose CpG islands would be most likely to be highly methylated, by comparing gene expression levels between seventy-six cases of tumor tissues and sixteen cases of non-tumor tissues which were excised from liver cancer patients by surgery, furthermore, chose twenty-three liver cancer specific methylation gene candidates actually carrying CpG islands in their promoter regions. Next, two liver cancer specific methylation gene candidates were selected by performing methylation analysis on genomic DNA derived from tumor tissues which were excised from liver cancer patients in early stage for said gene candidates. Furthermore, by confirming that liver cancer-derived methylation DNA fragments specific to said two genes in blood of liver cancer patients were detected, said two genes (BASP1 (Brain abundant, membrane attached signal protein 1) gene and SRD5A2 (Steroid-5-alpha-reductase, alpha polypeptide 2) gene) have been finally identified as liver cancer specific methylation genes.

Both said two genes, BASP1 gene and SRD5A2 gene, have been already cloned, and their cDNA (mRNA) sequences have been registered in the GenBank (BASP1:NM__006317, SRD5A2:NM__000348). However, there have been no indications that the CpG islands of said two genes were highly methylated in a cancer-specific manner. The inventors of the instant invention are the first ones who surprisingly experienced that said two genes are highly methylated in tumor liver tissues but rarely in non-tumor liver tissues. Namely, they found out that said two genes are highly methylated in a liver cancer-specific manner and are suitable as markers for detection of liver cancer.

Meanwhile, for twelve genes whose abnormal liver cancer specific methylations have been reported in previously published references, nine liver cancer specific methylation gene candidates were selected by performing methylation analysis on genomic DNA derived from tumor tissues which were excised from liver cancer patients in early stage. Furthermore, by confirming that liver cancer-derived methylation DNA fragments specific to five out of said nine genes in blood of liver cancer patients were detected, said five genes (SPINT2 (Serine protease inhibitor, kunitz-type, 2) gene, APC (Adenomatosis polyposis coli) gene, CCND2 (Cyclin D2) gene, CFTR (Cystic fibrosis transmembrane conductance regulator, ATP-binding cassette) gene and RASSF1 (Ras association (RalGDS/AF-6) domain family 1) gene) have been finally identified as liver cancer specific methylation genes.

All of said five genes, SPINT gene, APC gene, CCND2 gene, CFTR gene and RASSF1 gene, have been already cloned, and their cDNA (mRNA) sequences have been registered in the GenBank (SPINT2:NM__021102, APC:NM__000038, CCND2:NM__001759, CFTR:NM__000492, RASSF1:NM__007182). There have been some reports that the CpG islands of said five genes were highly methylated in a liver cancer-specific manner, but their methylation frequencies were various and there were no reports in HCV-positive liver cancer. The knowledge that said five genes are highly methylated in HCV-positive liver tumor liver tissues but rarely in non-tumor liver tissues, has been found out for the first time by the inventors. Namely, they found out that said five genes are highly methylated in a HCV-positive liver cancer-specific manner and are suitable as markers for detection of liver cancer, especially HCV-positive liver cancer.

A cancer to be detectable by the instant invention is preferably liver cancer, more preferably hepatocellular carcinoma (HCC) and the most preferably HCV-positive HCC. In this invention, detection of liver cancer means judging whether a subject is suspected to have liver cancer or not. When a subject has been suspected to have liver cancer, liver cancer is definitely diagnosed by diagnostic imaging and a pathological test.

According to the present invention detection of a risk of liver cancer means judging whether it is highly possible or not that a subject will develop liver cancer in the near future.

According to the present invention detection of recurrence of liver cancer means judging whether there is a probability or not that a subject will relapse to liver cancer after treatment of liver cancer.

According to the present invention detection of malignancy of liver cancer means judging whether liver cancer developing in a subject is highly malignant or not.

According to the present invention monitoring of progression of liver cancer with time means judging whether liver cancer developing in a subject is progressing with time or not.

Furthermore, the present invention is directed to a method which utilizes clinical specimens and detects liver cancer by identifying and/or quantifying methylation on BASP1 gene and/or SRD5A2 gene, or their DNA fragments in said specimens, or on at least two out of the above seven genes of BASP1 gene, SRD5A2 gene, SPINT2 gene, APC gene, CCND2 gene, CFTR gene and RASSFI gene, or their DNA fragments in said specimens. Combinations comprising three or more genes are preferably used, while BASP1 gene, SRD5A2 gene or SPINT2 gene are more preferably used according to the invention.

According to the present invention it is possible to utilize by combining concentration values in blood of conventionally used tumor marker proteins and/or free floating DNA amount in blood with identified results and/or quantified values of methylated cytosine on said seven genes. Conventionally used tumor marker proteins are preferably AFP and/or PIVKA-II, in particular AFP. Free floating DNA amount is preferably that measured for GSTP1 gene. DNAs before or after bisulfite (BIS) treatment can be used for measured DNA, wherein DNA after BIS treatment is preferably used.

Clinical specimens are in principle not limited, as far as they are obtained from subjects. For example, sera, plasma, whole blood, tissues, blood cells, excretions or internal/external secretion are applicable according to the invention. Sera, plasma and whole blood are preferably, and sera are in particular preferably used. Biopsy and tissues by surgical excision are suitable as tissues, feces and urine are suitable as excretions, and bile and pancreatic juice are suitable as internal/external secretion samples.

Subjects or patients are not limited as well, as far as they are human. The present invention is preferably applied to high risk patients of liver cancer (chronic hepatitis and liver cirrhosis), and in particular to HCV-positive high risk patients of liver cancer or liver cancer patients. Patients having suffered from liver cancer and experienced appropriate therapies may be included in high risk patients of liver cancer.

(2) Identification and/or Quantification of Methylation

According to the present invention "identification and/or quantification of methylation on particular genes" means identifying methylation at cytosine residues contained within CpG dinucleotides on CpG islands in promoter regions of particular genes in clinical specimens and/or quantifying a level of said methylation.

Methods for identification and/or quantification of methylation are methylation specific PCR (MSP) (see nonpatent literature 11) and/or HM-PCR (HeavyMethyl PCR) (see nonpatent literature 12) preferably, and are TaqMan-MSP and/or TaqMan-HM-PCR (see nonpatent literature 13) with TaqMan probes particularly preferably. For amplification reagents, a self-prepared reagent according to a public method may be used, and the LightCycler® TaqMan Master Kit (Roche Diagnostics GmbH) is preferably used.

The MSP means a method according to the invention, wherein at least either nucleotide sequence of a pair of PCR primers is complementary to a nucleotide sequence in the genomic DNA on a region containing cytosine residues which can undergo methylation, and can specifically hybridize to said nucleotide sequence in the genomic DNA when said cytosines are methylated. In particular, when cytosines which can undergo methylation are methylated, PCR amplification with PCR primers which can specifically hybridize to nucleotide sequence containing said methylated cytosines is carried out, and the absence or presence of methylation is detected depending on the absence or presence of said amplification. The HM-PCR means a method according to the invention, wherein at least either of a pair of PCR primers can specifically hybridize to a region containing no cytosine residues which can undergo methylation and oligonucleotide for blocking of amplification by said PCR primers are used simultaneously, which nucleotide sequences of said oligonucleotides partly overlap with nucleotide sequences of said PCR primers, are complementary to nucleotide sequences in the genomic DNA on a region containing cytosine residues which can undergo methylation at other parts and said oligonucleotides can specifically hybridize to said nucleotide sequences in the genomic DNA when said cytosines are not methylated. In particular, PCR primers can specifically hybridize to nucleotide sequence containing no cytosine which can undergo methylation, namely methylation-unspecific PCR primers without dependence on methylation of cytosines, and oligonucleotides (blocking probes) suitable to block amplification by said PCR primers are used simultaneously.

Said blocking probes partly overlap with said PCR primers. Therefore, when said blocking probes hybridize to target nucleotide sequences, amplification is blocked because said PCR primers are not able to hybridize. Said blocking probes are complementary to nucleotide sequences containing cytosines which can undergo methylation at other parts, and can specifically hybridize to nucleotide sequence containing said unmethylated cytosines when said cytosines are unmethylated. Accordingly, amplification is carried out by said PCR primers and the absence or presence of methylation can be detected depending on the absence or presence of said amplification by said PCR primers, only when cytosines are methylated.

Furthermore, it is possible to apply other methods for identification and/or quantification of methylation according to the invention, e.g., sequencing analysis or mass spectrometry, whereby sequencing analysis using the Pyrosequencer (Biotage AG) is preferred.

According to the present invention it is necessary to extract DNA from clinical specimens for pre-treatment for identification and/or quantification of methylation on particular genes. For example, commercially available kits like the MagNA Pure LC DNA Isolation Kit I (Roche Diagnostics GmbH) or the QIAamp DNA Blood Midi Kit (QIAGEN GmbH), or a reagent prepared according to known methods may be used for DNA extraction. DNA extraction using the DNA Extractor SP Kit for Serum and Plasma (Wako Pure Chemical Industries, Ltd.) is preferably used.

Extracted DNA is treated with a bisulfite reagent and unmethylated cytosines on DNA are converted to uracil (BIS treatment). Commercially available kits like the EpiTect Bisulfite Kit (QIAGEN GmbH), the EZ DNA Methylation-Gold Kit (Zymo Research Corporation) or the DNA Modification Kit (Chemicon® International, Inc.), or a reagent prepared according to a known method may be used for BIS treatment.

DNA which unmethylated cytosines on DNA are converted to uracils by said BIS treatment is amplified regions including CpG islands by nucleic acid amplification method like PCR, and is confirmed that unmethylated cytosines are regularly converted to uracils using said amplified products.

In particular, it is performed by nucleic acid amplification using primers to amplify nucleotide sequences of methylated cytosines which are not converted to uracils by BIS treatment and of unmethylated cytosines which are converted to uracils, confirmation of said amplified products by electrophoresis and/or sequencing analysis of said amplified products.

Length of said amplified products can be normally below 1000 bp, is below 180 by preferably and is around 100 by particularly preferably. In this invention, preferred primer sets and length of amplified products by said primer sets are shown in Table 1.

TABLE 1

Primer sets for MSP amplification of liver cancer specific methylation genes

| Primer set | Sense primer | Antisense primer | Length of products (bp) |
|---|---|---|---|
| 1 | BASP1_MSF (SEQ IDNo. 1) | BASP1_MSR (SEQ IDNo. 2) | 96 |
| 2 | SPINT2_MSF (SEQ IDNo. 3) | SPINT2_MSR (SEQ IDNo. 4) | 118 |
| 3 | APC_MSF (SEQ IDNo. 5) | APC_MSR (SEQ IDNo. 6) | 127 |
| 4 | CCND2_MSF (SEQ IDNo. 6) | CCND2_MSR (SEQ IDNo. 8) | 85 |
| 5 | CFTR_MSF (SEQ IDNo. 7) | CFTR_MSR (SEQ IDNo. 10) | 139 |
| 6 | RASSF1_MSF (SEQ IDNo. 11) | RASSF1_MSR (SEQ IDNo. 12) | 75 |
| 7 | SRD5A2_MSF (SEQ IDNo. 13) | SRD5A2_MSR (SEQ IDNo. 14) | 93 |
| 8 | BASP1_F (SEQ IDNo. 15) | BASP1_R (SEQ IDNo. 16) | 458 |
| 9 | SPINT2_F (SEQ IDNo. 17) | SPINT2_R (SEQ IDNo. 18) | 361 |
| 10 | APC_F (SEQ IDNo. 19) | APC_R (SEQ IDNo. 20) | 479 |
| 11 | CCND2_F (SEQ IDNo. 21) | CCND2_R (SEQ IDNo. 22) | 427 |
| 12 | CFTR_F (SEQ IDNo. 23) | CFTR_R (SEQ IDNo. 24) | 445 |
| 13 | RASSF1_F (SEQ IDNo. 25) | RASSF1_R (SEQ IDNo. 26) | 410 |

TABLE 1-continued

Primer sets for MSP amplification of liver cancer specific methylation genes

| Primer set | Sense primer | Antisense primer | Length of products (bp) |
|---|---|---|---|
| 14 | SRD5A2_F (SEQ IDNo. 27) | SRD5A2_R (SEQ IDNo. 28) | 465 |
| 15 | SPINT2_HMF (SEQ IDNo. 29) | SPINT2_HMR (SEQ IDNo. 30) | 162 |

In the above nucleic acid amplification, TaqMan probes which enable to identify specifically and/or quantify methylated cytosines by real-time PCR with simultaneous use of primer sets 1 to 7 described in Table 1 are shown in Table 2. Those probes are labeled with two different fluorescent substances at 5'-end and 3'-end of them. The use of fluorescent substances is not limited, as far as there are two different fluorescent substances. The 5'-end is preferably labeled, e.g., with FAM and the 3'-end with TAMRA particularly.

TABLE 2

TaqMan probes in order to identify MSP amplified products of liver cancer specific methylation genes

| Primer set | TaqMan probe | Fluorescent label at 5'-end | Fluorescent label at 3'-end |
|---|---|---|---|
| 1 | BASP1_TMP (SEQ IDNo. 31) | FAM | TAMRA |
| 2 | SPINT2_TMP (SEQ IDNo. 32) | FAM | TAMRA |
| 3 | APC_TMP (SEQ IDNo. 33) | FAM | TAMRA |
| 4 | CCND2_TMP (SEQ IDNo. 34) | FAM | TAMRA |
| 5 | CFTR_TMP (SEQ IDNo. 35) | FAM | TAMRA |
| 6 | RASSF1_TMP (SEQ IDNo. 36) | FAM | TAMRA |
| 7 | SRD5A2_TMP (SEQ IDNo. 37) | FAM | TAMRA |
| 15 | SPINT2_TMP (SEQ IDNo. 32) | FAM | TAMRA |

In the above nucleic acid amplification, blocking probes which enable to identify specifically and/or quantify methylated cytosines by HM-PCR reaction with simultaneous use of primer set 15 described in Table 1 are shown in Table 3. Those blocking probes are protected with a labeled substance. A labeled substance is in principle not limited, as far as DNA extension reaction from said blocking probe can be blocked, and is preferably labeled with phosphate. Furthermore, said blocking probes can be used as a single reagent and both probes are preferably used at a time.

TABLE 3

Blocking probes for HM-PCR for liver cancer specific methylation genes

| Primer set | TaqMan probe | Label at 3'-end |
|---|---|---|
| 15 | SPINT2_HMBF (SEQ IDNo. 38) | Phosphate |
| 15 | SPINT2_HMBR (SEQ IDNo. 39) | Phosphate |

The instant invention is directed to the above primers and probes as well as to a method for detection of liver cancer, detection of risk of liver cancer, detection of recurrence after treatment of liver cancer, detection of malignancy of liver cancer and monitoring of progression of liver cancer with time. Furthermore, the present invention covers a kit and a reagent for detection of liver cancer, a reagent can include primers and probes and a kit can contain reagents for DNA extraction, BIS treatment and nucleic acid amplification therein. This invention covers an instrument system for detection of liver cancer, detection of risk of liver cancer, detection of recurrence after treatment of liver cancer, detection of malignancy of liver cancer and monitoring of progression of liver cancer with time that uses a method, a kit, a reagent, primers and probes for detection of liver cancer, detection of risk of liver cancer, detection of recurrence after treatment of liver cancer, detection of malignancy of liver cancer and monitoring of progression of liver cancer with time.

As persons skilled in the art can understand easily, some bases can be deleted from or added to the 5'-end of SEQ ID No.1 to 14 out of said primers within the scope which can amplify said seven genes cytosine-specifically methylated. And some bases can be deleted from or added to the 5'-end of SEQ ID No.15 to 30 out of said primers within the scope which can amplify said seven genes specifically. Accordingly, the primers in this invention include primers wherein some bases are deleted from or added to SEQ IDNo.1 to 30 within said scope. Some bases can be deleted from or added to the ends of said probes within the scope which can hybridize with nucleotide sequences including methylated cytosines in amplified products using SEQ ID No.1 to 14 and 29-30 out of said primers, namely retains the original hybridization specificity of said probes.

Accordingly, the probes in this invention include probes wherein some bases are deleted from or added to SEQ IDNo.31 to 37 within said scope. Furthermore, they comprise complementary strands of said probes. Some bases can be deleted from or added to the ends of said blocking probes within the scope which can block amplification by using primer set 15. Accordingly, the blocking probes in this invention include blocking probes which some bases are deleted from or added to SEQ IDNo.38 and 39 within said scope.

EXAMPLES

Next, this invention is explained in more detail by showing examples which are actually performed by using known samples. However, the scope which this invention extends is not limited to only these examples.

Example 1

Identification of Liver Cancer Specific Methylation Genes

Using "Affymetrix Human Genome U95A DNA Chips®", we selected one hundred and one genes whose expression level specifically and significantly reduced twice and over in tumor tissues, namely whose CpG islands would be most likely to be highly methylated, by comparing gene expression levels between seventy-six cases of tumor tissues and sixteen cases of non-tumor tissues which were excised from liver cancer patients by surgery. Furthermore, twenty-three liver cancer specific methylation gene candidates which actually have CpG islands in their promoter regions were selected from said genes.

Next, each 1 1 µg of tumor tissue genomic DNA which obtained from twenty cases of liver cancer patients in early stage (liver cancer whose stage classification is stage I or II, and tumor size is below 1.3 to 3.6 cm) was BIS-treated, the regions including CpG islands on the above twenty-three candidate genes using said BIS-treated DNA for a template were amplified by PCR and the methylation status was examined by direct-sequencing. Also, the methylation status in genomic DNAs from normal liver tissues and leukocytes were simultaneously analyzed for control samples. To be concrete, as a result of methylation analysis four genes which were highly methylated in the tumor tissues but not in normal liver tissues and leukocytes were chosen.

Furthermore, by methylation analysis with the same procedure in genomic DNAs from each a pair of tumor tissue and non-tumor tissue which were excised from liver of new twenty cases of liver cancer patients who were different from the above liver cancer patients for said four genes, two liver cancer specific methylation gene candidates which were highly methylated in said tumor tissue but not in non-tumor tissue were determined. Furthermore, by confirming that liver cancer derivative methylated DNA fragments specific to said two genes were detected in blood of liver cancer patients, said two genes (BASP1 gene and SRD5A2 gene) were finally identified as liver cancer specific methylation genes.

Meanwhile, we selected twelve genes whose abnormal liver cancer specific methylations have been reported in previously published references. Next, each 1 μg of tumor tissue genomic DNA which obtained from twenty cases of liver cancer patients in early stage (liver cancer whose stage classification is stage I or II, and tumor size is below 1.3 to 3.6 cm) was BIS-treated, the regions including CpG islands on the above twelve candidate genes using said BIS-treated DNA for a template were amplified by PCR and the methylation status was examined by direct-sequencing. Also, the methylation status in genomic DNAs from normal liver tissues and leukocytes were simultaneously analyzed for control samples. As a result of methylation analysis, nine genes which were highly methylated in the tumor tissues but not in normal liver tissues and leukocytes were chosen.

Furthermore, by methylation analysis with the same procedure in genomic DNAs from each a pair of tumor tissue and non-tumor tissue which were excised from liver of new twenty cases of liver cancer patients who were different from the above liver cancer patients for said nine genes, nine liver cancer specific methylation gene candidates which were highly methylated in said tumor tissue but not in non-tumor tissue were determined. Furthermore, by confirming that liver cancer derivative methylated DNA fragments specific to five out of said nine genes were detected in blood of liver cancer patients, said five genes (SPINT2 gene, APC gene, CCND2 gene, CFTR gene and RASSF1 gene) were finally identified as liver cancer specific methylation genes.

Example 2

Performance Evaluation of Liver Cancer Specific Methylation Genes with a Small Number of Cases The total DNA was extracted from 1 ml of serum collected from nine cases of HCV-positive liver cancer in early stage (well-differentiated liver cancer) and nineteen cases of HCV-positive high risk patients of liver cancer (chronic hepatitis and liver cirrhosis) using the DNA Extractor SP Kit for Serum and Plasma (Wako Pure Chemical Industries, Ltd.) and 50 μl of DNA solution was prepared.

Said DNA solution was BIS-treated using a self-prepared reagent and 50 μl of BIS-treated DNA solution was prepared. Next, each methylation specific PCR (MSP) for seven liver cancer specific methylation genes (BASP1 gene, SPINT2 gene, APC gene, CCND2 gene, CFTR gene, RASSF1 gene and SRD5A2 gene) was performed with 5 μl of said BIS-treated DNA solution. In said MSP, by adding TaqMan probe specific to each gene together, quantification of methylated DNA by real-time PCR was carried out. Quantification of methylated DNA was actually performed by the following procedure.

BASP1 Gene, SPINT2 Gene, CCND2 Gene, CFTR Gene and RASSF1 Gene

Real-time PCR was performed using the LightCycler® TaqMan Master Kit (Roche Diagnostics GmbH) for an amplification reagent and the LightCycler® II (Roche Diagnostics GmbH) for a nucleic acid amplification instrument. For each gene, 5 μl of BIS-treated DNA solution was added into the PCR reaction mixture which mixed the primer set and the TaqMan probe of concentrations shown in Table 4 into 1× Master mix, and PCR was carried out in a total volume of 20 μl.

For BASP1, SPINT2, CCND2 and RASSF1 genes, PCR amplification was carried out by initial denaturation at 95° C. for 10 min followed by 50 cycles of 95° C. for 10 s, 63° C. for 45 s and 72° C. for 5 s followed by warming of 40° C. for 30 s. As for CFTR gene, PCR amplification was performed by initial denaturation at 95° C. for 10 min followed by 50 cycles of 95° C. for 10 s and 64° C. for 60 s followed by warming of 40° C. for 30 s. Fluorescent signal was detected after extension reaction at 72° C. of each cycle.

Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: at 1000, 200, 40 and 4 pg/μl for BASP1, SPINT2, CCND2 and RASSF1 genes, and at 200, 50 and 20 pg/μl for CFTR gene). Furthermore, said methylated DNA quantity in solution was multiplied by 50 and was converted to methylated DNA quantity in 1 ml of serum. Said methylated DNA quantity in serum was utilized for statistical analysis and clinical evaluation.

TABLE 4

MSP reaction mixture composition for liver cancer specific methylation genes

| Gene | Primer set | | TaqMan probe | |
|---|---|---|---|---|
| | | Conc. (μM) | | Conc. (μM) |
| BASP1 | 1 | 0.25 | BASP1_TMP (SEQ IDNo. 31) | 0.1 |
| SPINT2 | 2 | 0.25 | SPINT2_TMP (SEQ IDNo. 32) | 0.1 |
| CCND2 | 4 | 0.25 | CCND2_TMP (SEQ IDNo. 34) | 0.1 |
| CFTR | 5 | 0.6 | CFTR_TMP (SEQ IDNo. 35) | 0.1 |
| RASSF1 | 6 | 0.25 | RASSF1_TMP (SEQ IDNo. 36) | 0.1 |

APC Gene and SRD5A2 Gene

Real-time PCR was performed using a self-prepared reagent for an amplification reagent and the LightCycler®2.0 (Roche Diagnostics GmbH) for a nucleic acid amplification instrument. For each gene, 5 μl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 μM dNTPs, 2.5% glycerol and 0.15 unit ZO5 (thermostable DNA polymerase) and PCR was carried out in a total volume of 20 μl. For APC gene, PCR amplification was carried out by initial denaturation at 95° C. for 2 min followed by 50 cycles of 95° C. for 10 s, 64° C. for 60 s and 72° C. for 5 s followed by warming of 40° C. for 30 s.

For SRD5A2 gene, PCR amplification was performed by initial denaturation at 95° C. for 2 min followed by 50 cycles of 95° C. for 15 s, 66° C. for 45 s and 72° C. for 5 s followed by warming of 40° C. for 30 s. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: at 200, 50, 20 and 4 pg/μl for APC gene, and at 200, 40, 10 and 4 pg/μl for SRD5A2 gene). Furthermore, said methylated DNA quantity in solution was multiplied by 50 and was converted to methylated DNA quantity in 1 ml of serum. Said methylated DNA quantity in serum was utilized for statistical analysis and clinical evaluation.

TABLE 5

MSP reaction mixture composition for liver cancer specific methylation genes

| Gene | Primer set Conc. (μM) | TaqMan probe | Conc. (μM) | 2M potassium acetate Amount (μl) | Aptamer48 Amount (μl) |
|---|---|---|---|---|---|
| APC | 3 | 0.5 | APC_TMP (SEQ ID No. 33) | 0.25 | 1 | 0 |
| SRD5A2 | 7 | 0.4 | SRD5A2_TMP (SEQ ID No. 37) | 0.05 | 0.2 | 0.04 |

The Fisher ratio for each gene was calculated by a method reported by Iizuka et al. (see nonpatent literature 14) using methylated DNA quantity of said seven genes in the above nine cases of HCV-positive liver cancer patients in early stage and nineteen cases of HCV-positive high risk patients of liver cancer. The result is shown in Table 6. The higher Fisher ratio means more promising gene in this analyzed result. Therefore, it was shown that BASP1 gene was a promising gene particularly.

TABLE 6

Ranking of separability between liver cancer patients in early stage and high risk patients of liver cancer HCV carrier by the Fisher ratio

| Ranking | Gene | Fisher ratio |
|---|---|---|
| 1 | BASP1 | 1.10 |
| 2 | SPINT2 | 0.58 |
| 3 | CCND2 | 0.44 |
| 4 | SRD5A2 | 0.37 |
| 5 | APC | 0.31 |
| 6 | RASSF1 | 0.26 |
| 7 | CFTR | 0.12 |

For the top four genes of the Fisher ratio ranking by ROC (receiver operating characteristic) analysis, the performance was evaluated by examining the ability of said genes to detect liver cancer in early stage. Performances with two genes combination of the top two genes, BASP1 gene and SPINT2 gene, and with three genes combination of the top two genes and the forth gene, BASP1 gene, SPINT2 gene and SRD5A2 gene, were also assessed together. In particular, ROC analysis was directly carried out using methylated DNA quantity of each gene (methylated DNA quantity of BASP1 gene is designated as BASP1 value, and that of other genes is designated as well.) for a single gene, and was performed using values which were calculated with inputting said methylated DNA quantity into a formula: BASP1 value+SPINT2 value for two genes combination, and into a formula: 0.1×BASP1 value+SPINT2 value+SRD5A2 value for three genes combination, respectively.

The results are shown in FIG. 1. As a result of the above ROC analysis, while there were no genes which have enough performance to detect liver cancer in early stage with a single gene, enough high performance to detect liver cancer in early stage was shown by combining two or three genes. In particular, it was possible to detect liver cancer in early stage with sensitivity 78% and specificity 95% in combination with BASP1 genes and SPINT2 gene, and with sensitivity 89% and specificity 90% in combination with BASP1 genes, SPINT2 gene and SRD5A2 gene. Consequently, it has been suggested that measurement of methylated DNA amounts on liver cancer specific methylation genes which have been discovered in this invention is useful for detection of liver cancer in early stage.

Example 3

Performance Evaluation of Liver Cancer Specific Methylation Genes with a Large Number of Cases The total DNA was extracted from 1 ml of serum collected from one hundred and nineteen cases of HCV-positive liver cancer patients (including twenty-five cases of liver cancer in early stage whose stage classification is stage I (stage based on The General Rules for the Clinical and Pathologic Study of Primary Liver Cancer, see nonpatent literature 15) and tumor size is below 3 cm, and twenty-one cases of liver cancer in early stage that is well-differentiated) and eighty cases of HCV-positive high risk patients of liver cancer (chronic hepatitis and liver cirrhosis) using the DNA Extractor SP Kit for Serum and Plasma (Wako Pure Chemical Industries, Ltd.) and 50 μl of DNA solution was prepared. Said DNA solution was BIS-treated using a self-prepared reagent and 50 μl of BIS-treated DNA solution was prepared.

Next, each methylation specific PCR (MSP) for seven liver cancer specific methylation genes (BASP1 gene, SPINT2 gene, APC gene, CCND2 gene, CFTR gene, RASSF1 gene and SRD5A2 gene) was performed with 5 μl of said BIS-treated DNA solution. In said MSP, by adding TaqMan probe specific to each gene together, quantification of methylated DNA by real-time PCR was carried out. Meanwhile, according to the method described in patent literature 1, the total DNA amount in 1 ml of serum was measured with 1 μl of said BIS-treated DNA solution at the same time. Quantification of methylated DNA was actually performed by the following procedure.

BASP1 Gene, SPINT2 Gene, CCND2 Gene, CFTR Gene and RASSF1 Gene

Real-time PCR was performed using the LightCycler® TaqMan Master Kit (Roche Diagnostics GmbH) for an amplification reagent and the LightCycler® II (Roche Diagnostics GmbH) for a nucleic acid amplification instrument. For each gene, 5 µl of BIS-treated DNA solution was added into the PCR reaction mixture which mixed the primer set and the TaqMan probe of concentrations shown in Table 4 into 1× Master mix, and PCR was carried out in a total volume of 20 µl. For BASP1, SPINT2, CCND2 and RASSF1 genes, PCR amplification was carried out by initial denaturation at 95° C. for 10 min followed by 50 cycles of 95° C. for 10 s, 63° C. for 45 s and 72° C. for 5 s followed by warming of 40° C. for 30 s. As for CFTR gene, PCR amplification was performed by initial denaturation at 95° C. for 10 min followed by 50 cycles of 95° C. for 10 s and 64° C. for 60 s followed by warming of 40° C. for 30 s.

Fluorescent signal was detected after extension reaction at 72° C. of each cycle. Amplification of target gene was monitored by F1/F3 analysis mode in LightCycler software (Roche Diagnostics GmbH), and methylated DNA in 50 µl of BIS-treated DNA solution was quantified using the standard curve which was made with simultaneously measured standards (dilution series of artificially methylated DNA: at 1000, 200, 40 and 4 pg/µl for BASP1, SPINT2, CCND2 and RASSF1 genes, and at 200, 50 and 20 pg/µl for CFTR gene). Furthermore, said methylated DNA quantity in solution was multiplied by 50 and was converted to methylated DNA quantity in 1 ml of serum. Said methylated DNA quantity in serum was utilized for statistical analysis and clinical evaluation.

APC Gene and SRD5A2 Gene

Real-time PCR was performed using a self-prepared reagent for an amplification reagent and the LightCycler®2.0 (Roche Diagnostics GmbH) for a nucleic acid amplification instrument. For each gene, 5 µl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 µM dNTPs, 2.5% glycerol and 0.15 unit ZO5 (thermostable DNA polymerase) and PCR was carried out in a total volume of 20 µl. For APC gene, PCR amplification was carried out by initial denaturation at 95° C. for 2 min followed by 50 cycles of 95° C. for 10 s, 64° C. for 60 s and 72° C. for 5 s followed by warming of 40° C. for 30 s.

For SRD5A2 gene, PCR amplification was performed by initial denaturation at 95° C. for 2 min followed by 50 cycles of 95° C. for 15 s, 66° C. for 45 s and 72° C. for 5 s followed by warming of 40° C. for 30 s. Amplification of target gene was monitored by F1/F3 analysis mode in LightCycler software (Roche Diagnostics GmbH), and methylated DNA in 50 µl of BIS-treated DNA solution was quantified using the standard curve which was made with simultaneously measured standards (dilution series of artificially methylated DNA: at 200, 50, 20 and 4 pg/µl for APC gene, and at 200, 40, 10 and 4 pg/µl for SRD5A2 gene). Furthermore, said methylated DNA quantity in solution was multiplied by 50 and was converted to methylated DNA quantity in 1 ml of serum. Said methylated DNA quantity in serum was utilized for statistical analysis and clinical evaluation.

The Fisher ratio for each gene was calculated by a method reported by Iizuka et al. (see nonpatent literature 14) using methylated DNA quantity of said seven genes in the above one hundred and nineteen cases of HCV-positive liver cancer patients and eighty cases of high risk patients of liver cancer. The result is shown in Table 7. The higher Fisher ratio means more promising gene in this analyzed result. Therefore, it was shown that BASP1 gene and SPINT2 gene were promising genes, and BASP1 gene was a promising gene particularly.

ROC analysis was performed using methylated DNA quantity for said BASP1 gene and SPINT2 gene. Consequently, it was possible to detect liver cancer with sensitivity 50% and specificity 95% or sensitivity 62% and specificity 80% with only said BASP1 gene, and with sensitivity 38% and specificity 96% with only said SPINT2 gene. Consequently, it has been suggested that measurement of methylated DNA amounts on BASP1 gene and/or SPINT2 gene out of liver cancer specific methylation genes which have been discovered in this invention is useful for detection of liver cancer.

TABLE 7

Ranking of separability between liver cancer patients and high risk patients of liver cancer HCV carrier by the Fisher ratio

| Ranking | Gene | Fisher ratio |
| --- | --- | --- |
| 1 | BASP1 | 0.0704 |
| 2 | CFTR | 0.0412 |
| 3 | SPINT2 | 0.0365 |
| 4 | RASSF1 | 0.0344 |
| 5 | CCND2 | 0.0155 |
| 6 | SRD5A2 | 0.0145 |
| 7 | APC | 0.0110 |

Next, performances of said genes combination were evaluated by examining the ability to detect liver cancer in combination with three out of said seven genes using FLC (Fisher linear classifier) analysis for one hundred and nineteen cases of liver cancer patients, twenty-five cases of liver cancer in early stage whose stage classification is stage I and tumor size is below 3 cm, or twenty-one cases of liver cancer in early stage that is well-differentiated. In particular, a data reduction algorithm was established using methylated DNA quantity of each gene by a method reported by Iizuka et al. (see nonpatent literature 14), sensitivity, specificity and recognition rate for detection of liver cancer were calculated using said algorithm, and ROC analysis was performed on the basis of results by said FLC analysis. The results are shown in FIGS. 2 to 4.

As a result of said FLC analysis and ROC analysis, it was possible to detect liver cancer with sensitivity 70%, specificity 80% and recognition rate 74% by a formula: 0.9586×BASP1 value+0.2843×SPINT2 value−0.0078×CFTR value+0.3180 (If a calculated value is <0, determined as liver cancer.) in combination with three genes of BASP1 gene, SPINT2 gene and CFTR gene for one hundred and nineteen cases of liver cancer patients.

It was possible to detect liver cancer in early stage with sensitivity 52%, specificity 88% and recognition rate 79% by a formula: −0.003091×BASP1 value−0.006448×SPINT2 value−0.000655×CCND2 value+0.350734 (If a calculated value is <0, determined as liver cancer.) in combination with three genes of BASP1 gene, SPINT2 gene and CCND2 gene for twenty-five cases of liver cancer in early stage whose stage classification is stage I and tumor size is below 3 cm. It was possible to detect liver cancer in early stage with sensitivity 67%, specificity 80% and recognition rate 77% by a formula: −0.009564×BASP1 value−0.004042×SPINT2 value−0.001373×RASSF1 value+0.595593 (If a calculated value is <0, determined as liver cancer.) in combination with three genes of BASP1 gene, SPINT2 gene and RASSF1 gene for twenty-one cases of liver cancer in early stage that is well-differentiated (Tables 8 to 10).

As shown in FIGS. 2 to 4, said ability to detect liver cancer exceeded that of AFP or PIVKA-II (e.g., HCC (n=115) vs. HCV carrier (n=57): AFP (cut-off 200); sensitivity 30%, specificity 100%, recognition rate 53%; PIVKA-II (cut-off 40%); sensitivity 60%, specificity 85%, recognition rate 68%), conventionally used tumor markers which were measured simultaneously. Consequently, it has been suggested that measurement of methylated DNA amounts on liver cancer specific methylation genes which have been discovered in this invention is useful for detection of liver cancer, especially liver cancer in early stage.

Furthermore, combining simultaneously measured AFP and PIVKA-II and the above seven genes into nine factors, performance of said factors combination was evaluated by examining the ability to detect liver cancer in combination with two or three out of said nine factors. As a result, it was possible to detect liver cancer with sensitivity 75%, specificity 82% and recognition rate 78% by a formula: $-0.000478 \times$ BASP1 value$-0.000011 \times$AFP value$+0.001089$ (If a calculated value is <0, determined as liver cancer.) in combination with two factors of BASP1 gene and AFP. It was also possible to detect liver cancer with sensitivity 79%, specificity 82% and recognition rate 80% by a formula: $-0.000476 \times$BASP1 value$-0.000017 \times$SPINT2 value$-0.000010 \times$AFP value$+0.001789$ (If a calculated value is <0, determined as liver cancer.) in combination with BASP1 gene, SPINT2 gene and AFP.

It was possible to detect liver cancer in early stage with sensitivity 60%, specificity 82% and recognition rate 74% by a formula: $-0.002106 \times$BASP1 value$-0.005210 \times$SPINT2 value$+0.000069 \times$PIVKA-II value$+0.001390$ (If a calculated value is <0, determined as liver cancer.) in combination with three markers of BASP1 gene, SPINT2 gene and PIVKA-II for twenty-five cases of liver cancer in early stage whose stage classification is stage I and tumor size is below 3 cm. It was possible to detect liver cancer in early stage with sensitivity 67%, specificity 88% and recognition rate 81% by a formula: $-0.002538 \times$APC value$-0.003626 \times$SPINT2 value$-0.013544 \times$AFP value$+0.852581$ (If a calculated value is <0, determined as liver cancer.) in combination with 3 markers of APC gene, SPINT2 gene and AFP for twenty-one cases of liver cancer in early stage that is well-differentiated (Tables 8 to 10). Consequently, it has been suggested that measurement of methylated DNA amounts on liver cancer specific methylation genes which have been discovered in this invention, and combination with said measured values and conventionally used tumor marker AFP or PIVKA-II can further increase the ability to detect liver cancer, especially liver cancer in early stage.

Furthermore, combining simultaneously measured DNA amounts in serum, AFP, PIVKA-II and the above seven genes into ten factors, performance of said factors combination was evaluated by examining the ability to detect liver cancer in combination with three out of said ten factors. As a result, it was possible to detect liver cancer with sensitivity 87%, specificity 80% and recognition rate 85% by a formula: $-0.000219 \times$BASP1 value$-0.000016 \times$SPINT2 value$-0.015627 \times$DNA amounts in serum$+0.618672$ (If a calculated value is <0, determined as liver cancer.) in combination with BASP1 gene, SPINT2 gene and DNA amounts in serum, a formula: $-0.000220 \times$BASP1 value$-0.000564 \times$SRD5A2 value$-0.015633 \times$DNA amounts in serum$+0.613763$ (If a calculated value is <0, determined as liver cancer.) in combination with BASP1 gene, SRD5A2 gene and DNA amounts in serum, and a formula: $-0.000224 \times$BASP1 value$-0.000010 \times$ AFP value$-0.015610 \times$DNA amounts in serum$+0.617716$ (If a calculated value is <0, determined as liver cancer.) in combination with BASP1 gene, AFP and DNA amounts in serum.

It was possible to detect liver cancer in early stage with sensitivity 84%, specificity 88% and recognition rate 86% by a formula: $-0.021150 \times$SRD5A2 value$-0.007102 \times$SPINT2 value$-0.052594 \times$DNA amounts in serum$+2.091284$ (If a calculated value is <0, determined as liver cancer.) in combination with three markers of SDR5A2 gene, SPINT2 gene and DNA amounts in serum for twenty-five cases of liver cancer in early stage whose stage classification is stage I and tumor size is below 3 cm. It was possible to detect liver cancer in early stage with sensitivity 86%, specificity 90% and recognition rate 89% by a formula: $-0.001553 \times$SRD5A2 value$-0.002923 \times$SPINT2 value$-0.029064 \times$DNA amounts in serum$+1.305493$ (If a calculated value is <0, determined as liver cancer.), a formula: $-0.003378 \times$SPINT2 value$-0.009112 \times$AFP value$-0.027178 \times$DNA amounts in serum$+1.393957$ (If a calculated value is <0, determined as liver cancer.) and a formula: $-0.002833 \times$SPINT2 value$+0.000061 \times$PIVKA-II value$-0.029513 \times$DNA amounts in serum$+1.384308$ (If a calculated value is <0, determined as liver cancer.) in combination with three markers of SRD5A2 gene, SPINT2 gene and DNA amounts in serum, three markers of SPINT2 gene, AFP and DNA amounts in serum, and three markers of SPINT2 gene, PIVKA-II and DNA amounts in serum for twenty-one cases of liver cancer in early stage that is well-differentiated (Tables 8 to 10).

Consequently, it has been suggested that measurement of methylated DNA amounts on liver cancer specific methylation genes which have been discovered in this invention, and combination with said measured values and DNA amounts in serum, with said measured values, DNA amounts in serum and AFP values, or with said measured values, DNA amounts in serum and PIVKA-II values can further increase the ability to detect liver cancer, especially liver cancer in early stage.

TABLE 8

Ability to detect liver cancer by combining liver cancer specific
methylation genes, conventionally used tumor markers
and DNA amount in blood
HCC 119 cases

| Combination of factos | | | Sensitivity (%) | Specificity (%) | Recognition Rate (%) | Classifier | |
|---|---|---|---|---|---|---|---|
| 7 methylated DNA markers(Selection out of 7 markers) | | | | | | | |
| CFTR | BASP1 | SPINT2 | 70 | 80 | 74 | $-0.958600 \times$ BASP1 $- 0.284300 \times$ SPINT2 $+ 0.007800 \times$ CFTR $+ 0.318000$ | If < 0, determined as HCC |
| 2 conventional markers + 7 methylated DNA markers(Selection out of 9 markers) | | | | | | | |
| AFP | BASP1 | SPINT2 | 79 | 82 | 80 | $-0.000476 \times$ BASP1 $- 0.000017 \times$ SPINT2 $- 0.000010 \times$ AFP $+ 0.001789$ | If < 0, determined as HCC |
| AFP | BASP1 | | 75 | 82 | 78 | $-0.000478 \times$ BASP1 $- 0.000011 \times$ AFP $+ 0.001089$ | If < 0, determined as HCC |

TABLE 8-continued

Ability to detect liver cancer by combining liver cancer specific
methylation genes, conventionally used tumor markers
and DNA amount in blood
HCC 119 cases

| Combination of factos | | | Sensitivity (%) | Specificity (%) | Recognition Rate (%) | Classifier | |
|---|---|---|---|---|---|---|---|
| DNA amount + 2 conventional markers + 7 methylated DNA markers(Selection out of 10 markers) | | | | | | | |
| DNA | BASP1 | SPINT2 | 87 | 80 | 85 | $-0.000291 \times$ BASP1 $- 0.000016 \times$ SPINT2 $- 0.015627 \times$ DNA $+ 0.618672$ | If < 0, determined as HCC |
| DNA | BASP1 | SRD5A2 | 87 | 80 | 85 | $-0.000220 \times$ BASP1 $- 0.000564 \times$ SRD5A2 $- 0.015633 \times$ DNA $+ 0.613763$ | If < 0, determined as HCC |
| DNA | AFP | BASP1 | 87 | 80 | 85 | $-0.000224 \times$ BASP1 $- 0.000010 \times$ AFP $- 0.015610 \times$ DNA $+ 0.617716$ | If < 0, determined as HCC |

TABLE 9

Ability to detect liver cancer by combining liver cancer specific
methylation genes, conventionally used tumor markers
and DNA amount in blood
Early HCC (TNM classification state I and tumor size below 3 cm) 25 cases

| Combination of factos | | | Sensitivity (%) | Specificity (%) | Recognition Rate (%) | Classifier | |
|---|---|---|---|---|---|---|---|
| 7 methylated DNA markers(Selection out of 7 markers) | | | | | | | |
| CCND2 | BASP1 | SPINT2 | 52 | 88 | 79 | $-0.003091 \times$ BASP1 $- 0.006448 \times$ SPINT2 $- 0.000655 \times$ CCND2 $+ 0.350734$ | If < 0, determined as HCC |
| 2 conventional markers + 7 methylated DNA markers(Selection out of 9 markers) | | | | | | | |
| PIVKA | BASP1 | SPINT2 | 60 | 82 | 74 | $+0.000069 \times$ PIVKA $- 0.002106 \times$ BASP1 $- 0.005210 \times$ SPINT2 $+ 0.001390$ | If < 0, determined as HCC |
| DNA amount + 2 conventional markers + 7 methylated DNA markers(Selection out of 10 markers) | | | | | | | |
| DNA | SRD5A2 | SPINT2 | 84 | 88 | 86 | $-0.052594 \times$ DNA $+ 0.021150 \times$ SRD5A2 $- 0.007102 \times$ SPINT2 $+ 2.091284$ | If < 0, determined as HCC |

TABLE 10

Ability to detect liver cancer by combining liver cancer specific
methylation genes, conventionally used tumor markers
and DNA amount in blood
Early HCC (Well-differentiated) 21 cases

| Combination of factos | | | Sensitivity (%) | Specificity (%) | Recognition Rate (%) | Classifier | |
|---|---|---|---|---|---|---|---|
| 7 methylated DNA markers(Selection out of 7 markers) | | | | | | | |
| RASSF1 | BASP1 | SPINT2 | 67 | 80 | 77 | $-0.009564 \times$ BASP1 $- 0.004042 \times$ SPINT2 $- 0.001373 \times$ RASSF1 $+ 0.595593$ | If < 0, determined as HCC |
| 2 conventional markers + 7 methylated DNA markers(Selection out of 9 markers) | | | | | | | |
| AFP | APC | SPINT2 | 67 | 88 | 81 | $-0.013544 \times$ AFP $- 0.002538 \times$ APC $- 0.003626 \times$ SPINT2 $+ 0.852581$ | If < 0, determined as HCC |
| DNA amount + 2 conventional markers + 7 methylated DNA markers(Selection out of 10 markers) | | | | | | | |
| DNA | SRD5A2 | SPINT2 | 86 | 90 | 89 | $-0.029064 \times$ DNA $- 0.001553 \times$ SRD5A2 $- 0.002923 \times$ SPINT2 $+ 1.305493$ | If < 0, determined as HCC |
| DNA | AFP | SPINT2 | 86 | 90 | 89 | $-0.009112 \times$ AFP $- 0.027178 \times$ DNA $- 0.003378 \times$ SPINT2 $+ 1.393957$ | If < 0, determined as HCC |
| DNA | PIVKA | SPINT2 | 86 | 90 | 89 | $+0.000061 \times$ PIVKA $- 0.029513 \times$ DNA $- 0.002833 \times$ SPINT2 $+ 1.324308$ | If < 0, determined as HCC |

Example 4

Methylated DNA Quantification by Quantitative Direct Sequencing

For the above seven liver cancer specific methylation genes, BASP1 gene, SRD5A2 gene, SPINT2 gene, APC gene, CCND2 gene, CFTR gene and RASSF1 gene, methylation analysis on regions including CpG islands in a pair of tumor and non-tumor tissue genomic DNAs which was excised from livers of liver cancer patients twenty cases was performed by quantitative direct sequencing.

In particular, 1 μg of genomic DNA extracted from tissues was BIS-treated and the regions including CpG islands on the above seven genes using said BIS-treated DNA for a template were amplified by PCR with primer sets described in Table 11. The PCR reaction solution was composed of 26.7 ng of BIS-treated DNA, two units of thermostable DNA polymerase (TOYOBO CO., LTD) which was pretreated with the equal volume of TaqStart™ Antibody (Clontech Laboratories, Inc.) for 5 min at room temperature, 67 mM Tris-HCl (pH 8.8), 16.6 mM ammonium sulfate, 0.01% Tween 20, 200 µM dNTPs, each 1 µM of a primer pair, and 1.5 or 3 mM magnesium chloride in a final volume of 100 µl.

DNA amplification was performed by using GeneAmp PCR system 9600 (Applied Biosystems) as a PCR amplification instrument by initial denaturation at 95° C. for 2 min followed by 5 cycles of denaturation at 95° C. for 25 s, annealing at 70° C. for 45 s, extension at 72° C. for 45 s, and followed by 40 cycles of denaturation at 95° C. for 25 s, annealing at 65° C. for 50 s, extension at 72° C. for 45 s. The PCR products were concentrated, and subjected to electrophoresis on agarose gel. The target bands of amplified products were excised from gel and isolated using the QIAquick Gel Extraction Kit (QIAGEN GmbH). Next, the methylation status in regions including CpGs was examined by quantitative directsequencing using Pyrosequencer PSQ96MA and Pyro gold Reagents (Biotage AG) with the said isolated products as a template.

TABLE 11

PCR reaction composition to amplify regions including CpG islands of liver cancer specific methylation genes

| Gene | Primer set | Magnesium chloride concentration (mM) |
|---|---|---|
| BASP1 | 8 | 1.5 |
| SPINT2 | 9 | 1.5 |
| APC | 10 | 1.5 |
| CCND2 | 11 | 1.5 |
| CFTR | 12 | 1.5 |
| RASSF1 | 13 | 1.5 |
| SRD5A2 | 14 | 3 |

Results of methylation analysis by quantitative directsequencing are shown in Tables 12 to 14. Methylation quantities are shown by appending "* (3 asterisks)", " (2 asterisks)", "* (an asterisk)", and no asterisk in case over 75%, below 75% and over 50%, below 50% and over 25%, and below 25%, respectively. As shown in Tables 12 to 14, it was possible to distinguish definitely between tumor tissues, and non-tumor tissues of liver cancer patients and tissues of HCV carriers (high risk patients of liver cancer) by performing quantitative methylation analysis of regions including CpG islands on the above seven liver cancer specific methylation genes.

Namely it was shown that methylation analysis of regions including CpG islands on the said seven liver cancer specific methylation genes in liver tissue DNAs by the said quantitative sequencing was useful for identification and discrimination of liver cancer. Furthermore, compared the methylated DNA amount of CFTR gene shown in Tables 12 to 14 between well differentiated HCC and poorly differentiated HCC, the stage of differentiation (malignancy) correlated positively with the methylated DNA amount ($p<0.05$). Thus, it was suggested that quantitative methylation analysis would be usable as an indicator of malignancy of liver cancer.

TABLE 12

Results of methylation analysis by quantitative direct sequencing
Liver cancer patinets/tumor tissues

| ID | Differentiation type | HCV/HBV infection | tumor size (cm) | TMN classification Stage | Methylated DNA quantity (%) | | | | | | |
|---|---|---|---|---|---|---|---|---|---|---|---|
| | | | | | BASP1 | SPINT2 | APC | CCND2 | CFTR | RASSF1 | SRD5A2 |
| 1 | Well | HCV | 2.4 | II | 27.6* | 37.2* | 57.7** | 43.8* | 20.3 | 41.7* | 23.6 |
| 2 | Well | HCV | 3.5 | III | 34.7* | 40.4* | 63.3** | 57.1** | 36.6* | 44.5* | 24.8 |
| 3 | Well | HCV | 3.4 | II | 31.1* | 31.7* | 53.8** | 48.8* | 42.8* | 48.2* | 27.2* |
| 4 | Moderate | — | 16 | IV | 42.5* | 48.0* | 36.1* | 46.9* | 62.1** | 60.9** | 48.3* |
| 5 | Moderate | HCV | 3 | II | 36.4* | 9.7 | 62.1** | 40.3* | 30.9* | 49.1* | 20.1 |
| 6 | Moderate | — | 2.5 | II | 34.8* | 16.3 | 42.1* | 35.4* | 36.6* | 29.8* | 21.4 |
| 7 | Moderate | HCV | 4.2 | II | 31.4* | 28.2* | 50.0** | 40.5* | 24.8 | 39.6* | 35.8* |
| 8 | Well | HCV | 1.8 | I | 33.7* | 22.1 | 61.7** | 49.9 | 44.9* | 55.0** | 49.5* |
| 9 | Moderate | HCV/HBV | 3.4 | IV | 42.4* | 39.9* | 68.1** | 67.8** | 29.3* | 64.7** | 48.1* |
| 10 | Well | HCV | 1.4 | I | 34.6* | 20.6 | 14.3 | 41.3* | 31.3* | 55.9** | 20.6 |
| 11 | Well | HCV | 3.7 | II | 25.7* | 9.0 | 32.7* | 18.3 | 22.7 | 21.4 | 32.9* |
| 12 | Well | HCV | 5.4 | III | 55.6** | 56.0** | 69.4** | 41.5* | 68.8** | 60.3** | 28.7* |
| 13 | Moderate | HCV | 1.2 | I | 30.3* | 39.4* | 51.4** | 50.6** | 33.4* | 46.9* | 23.7 |
| 14 | Moderate | HCV | 8.1 | II | 26.7* | 48.7* | 60.9** | 45.1* | 60.2** | 59.3** | 32.8* |
| 15 | Moderate | — | 3.5 | III | 18.5 | 16.5 | 21.1 | 30.3* | 16.8 | 28.8* | 28.8* |
| 16 | Well | HCV/HBV | 2.4 | II | 21.1 | 24.4 | 33.2* | 39.3* | 32.1* | 37.2* | 36.4* |
| 17 | Well | HBV | 2.3 | III | 22.4 | 23.8 | 31.6* | 37.4* | 26.8* | 53.7** | 27.4* |
| 18 | Moderate | HCV | 4.5 | III | 34.3* | 48.7* | 72.2*** | 78.5*** | 45.4* | 66.6** | 19.4 |
| 19 | Well | HCV | 3.8 | III | 41.3* | 44.0* | 57.6** | 60.8** | 43.9* | 54.7** | 47.3* |
| 20 | Poor | HCV | 1.2 | III | 34.3* | 42.2* | 53.8** | 46.3* | 56.2** | 54.9** | 47.6* |

TABLE 13

Results of methylation analysis by quantitative direct sequencing
Liver cancer patinets/non-tumor tissues

| ID | Differentiation type | HCV/HBV infection | tumor size (cm) | TMN classification Stage | Methylated DNA quantity (%) | | | | | | |
|---|---|---|---|---|---|---|---|---|---|---|---|
| | | | | | BASP1 | SPINT2 | APC | CCND2 | CFTR | RASSF1 | SRD5A2 |
| 1 | Well | HCV | 2.4 | II | 23.2 | 8.0 | 24.3 | 32.0* | 18.0 | 19.5 | 20.8 |
| 2 | Well | HCV | 3.5 | III | 28.1* | 7.5 | 16.1 | 17.9 | 20.1 | 19.3 | 18.9 |
| 3 | Well | HCV | 3.4 | II | 25.6* | 6.3 | 17.3 | 30.5* | 22.7 | 12.5 | 18.0 |
| 4 | Moderate | — | 16 | IV | 29.2* | 12.6 | 31.1* | 25.7* | 17.4 | 39.7* | 22.2 |
| 5 | Moderate | HCV | 3 | II | 20.4 | 6.9 | 18.6 | 22.3 | 15.1 | 28.2* | 17.4 |
| 6 | Moderate | — | 2.5 | II | 29.5* | 6.7 | 15.4 | 22.1 | 9.2 | 23.8 | 15.9 |
| 7 | Moderate | HCV | 4.2 | II | 20.8 | 9.2 | 17.7 | 25.7* | 14.1 | 18.8 | 23.0 |
| 8 | Well | HCV | 1.8 | I | 23.7 | 9.1 | 16.6 | 21.1 | 16.2 | 27.8* | 19.2 |
| 9 | Moderate | HCV/HBV | 3.4 | IV | 24.7 | 11.2 | 21.3 | 36.7* | 23.0 | 22.9 | 26.5* |
| 10 | Well | HCV | 1.4 | I | 29.2* | 10.6 | 23.8 | 19.8 | 14.9 | 33.3* | 21.9 |
| 11 | Well | HCV | 3.7 | II | 27.6* | 6.9 | 13.3 | 24.8 | 17.8 | 18.5 | 21.1 |
| 12 | Well | HCV | 5.4 | III | 19.6 | 10.0 | 14.6 | 19.0 | 21.4 | 19.9 | 21.8 |
| 13 | Moderate | HCV | 1.2 | I | 21.0 | 9.4 | 18.6 | 24.8 | 21.3 | 19.9 | 17.5 |
| 14 | Moderate | HCV | 8.1 | II | 20.8 | 10.8 | 19.8 | 14.9 | 18.7 | 40.6* | 23.2 |
| 15 | Moderate | — | 3.5 | III | 22.8 | 11.1 | 15.2 | 28.5* | 14.4 | 37.7* | 21.2 |
| 16 | Well | HCV/HBV | 2.4 | II | 25.5* | 11.8 | 14.8 | 26.1* | 22.9 | 21.6 | 27.5* |
| 17 | Well | HBV | 2.3 | III | 17.8 | 10.7 | 18.8 | 20.7 | 17.5 | 19.9 | 24.8 |
| 18 | Moderate | HCV | 4.5 | III | 19.7 | 5.8 | 13.1 | 31.9* | 16.8 | 17.2 | 18.6 |
| 19 | Well | HCV | 3.8 | III | 21.4 | 11.1 | 11.9 | 27.8* | 20.0 | 16.0 | 24.7 |
| 20 | Poor | HCV | 1.2 | III | 19.0 | 9.4 | 14.8 | 42.7* | 15.0 | 24.7 | 25.3* |

TABLE 14

Results of methylation analysis by quantitative direct sequencing
HCV carrier (high risk patients of liver cancer)/liver tissues

| | | Methylated DNA quantity (%) | | | | | | |
|---|---|---|---|---|---|---|---|---|
| ID | HCV/HBV infection | BASP1 | SPINT2 | APC | CCND2 | CFTR | RASSF1 | SRD5A2 |
| 21 | HCV | 16.9 | 9.4 | 13.0 | 30.7* | 20.1 | 23.5 | 19.2 |
| 22 | HCV | 17.4 | 9.4 | 16.4 | 37.2* | 18.3 | 28.3* | 23.7 |

Example 5

Methylated DNA Quantification by HM (Heavy-Methyl)-PCR

Of the above seven liver cancer specific methylation genes, for SPINT2 gene, methylation analysis on the region containing CpG islands in tumor tissue genomic DNA which obtained from ten cases of liver cancer patients and in non-tumor tissue genomic DNA which obtained from nine cases of liver cancer patients, carried out by HM-PCR. In particular, 1 μg of genomic DNA extracted from tissues was BIS-treated and 75 μl of BIS-treated DNA solution was prepared. Next, HM-PCR was conducted using a primer set 15 (SEQ IDNo.29 and 30) and two blocking probes (SEQ IDNo.38 and 39) with 1 μl (13.3 ng) of said BIS-treated DNA solution for a template.

During said HM-PCR, methylated DNA quantification by real-time PCR was carried out using TaqMan probe (SEQ ID No.32) specific to SPINT2 gene. Real-time PCR was performed using the LightCycler® TaqMan Master Kit (Roche Diagnostics GmbH) for an amplification reagent and the LightCycler®2.0 (Roche Diagnostics GmbH) for a nucleic acid amplification instrument. One μl of BIS-treated DNA solution was added into the PCR reaction mixture which mixed 0.5 μM of the primer set, 20 μM of the blocking probes and 0.1 μM of the TaqMan probe into 1× Master mix, and PCR was carried out in a total volume of 20 μl. PCR amplification was carried out by initial denaturation at 95° C. for 10 min followed by 50 cycles of 95° C. for 10 s and 58° C. for 60 s followed by warming of 40° C. for 30 s.

Fluorescent signal was detected after extension reaction at 58° C. of each cycle. Amplification of target gene was monitored by F1/F3 analysis mode in LightCycler software (Roche Diagnostics GmbH), and methylated DNA concentration in 75 μl of BIS-treated DNA solution was calculated using the standard curve which was made with simultaneously measured standards (dilution series of artificially methylated DNA: at 1000, 200, and 40 pg/μl). As shown in Table 15, it was possible to discriminate between tumor and non-tumor tissues with sensitivity 80% and specificity 88.9% by using 100 pg/μl as a cut-off value. Consequently, it has been suggested that methylation analysis of the region containing CpG islands on a liver cancer specific methylation gene, SPINT2 gene, in liver tissue DNAs by HM-PCR is useful to detect and distinguish liver cancer.

TABLE 15

Results of methylation analysis by HM-PCR

| ID | Cp | Conc.(pg/μl) | Met (%) |
|---|---|---|---|
| HCC 1 | 31.91 | 5.98E+02 | 60.6 |
| HCC 5 | 32.55 | 3.95E+02 | 40.1 |
| HCC 6 | 33.51 | 2.13E+02 | 21.6 |
| HCC 7 | 32.09 | 5.34E+02 | 54.2 |
| HCC 11 | 33.35 | 2.36E+02 | 23.9 |
| HCC 12 | | | |
| HCC 27 | 34.15 | 1.41E+02 | 14.3 |

TABLE 15-continued

Results of methylation analysis by HM-PCR

| ID | Cp | Conc.(pg/µl) | Met (%) |
|---|---|---|---|
| HCC 43 | 34.55 | 1.09E+02 | 11.1 |
| HCC 64 | | | |
| HCC 119 | 34.27 | 1.30E+02 | 13.2 |
| non-HCC 1 | 39.54 | 4.32E+00 | 0.4 |
| non-HCC 5 | | | |
| non-HCC 6 | | | |
| non-HCC 7 | 33.19 | 2.61E+02 | 26.5 |
| non-HCC 12 | | | |
| non-HCC 27 | | | |
| non-HCC 43 | | | |
| non-HCC 64 | | | |
| non-HCC 119 | | | |
| std 5 ng | 31.14 | 9.86E+02 | 1000 |
| std 1 ng | 33.57 | 2.05E+02 | 200 |
| std 200 pg | 37.18 | 1.98E+01 | 40 |

CP: Crossing point
Met: Methylation rate

Example 6

Detection of a Risk of Liver Cancer by Measurement of Liver Cancer Specific Methylation Genes The total DNA was extracted from 1 ml of serum collected from thirty-one cases of HCV-positive liver cancer patients (patients who were taken a follow-up for over two years after collection of serum and curative resection of liver cancer) using the DNA Extractor SP Kit for Serum and Plasma (Wako Pure Chemical Industries, Ltd.) and 50 µl of DNA solution was prepared. Said DNA solution was BIS-treated using a self-prepared reagent and 50 µl of BIS-treated DNA solution was prepared.

Next, each methylation specific PCR (MSP) for seven liver cancer specific methylation genes (BASP1 gene, SPINT2 gene and SRD5A2 gene) was performed with 5 µl of said BIS-treated DNA solution. In said MSP, by adding TaqMan probe specific to each gene together, quantification of methylated DNA by real-time PCR was carried out. Meanwhile, according to the method described in patent literature 1, the total DNA amount in 1 ml of serum was measured with 1 µl of said BIS-treated DNA solution at the same time. Quantification of methylated DNA was actually performed by the following procedure.

BASP1 Gene and SPINT2 Gene

Real-time PCR was performed using the LightCycler® TaqMan Master Kit (Roche Diagnostics GmbH) for an amplification reagent and the LightCycler®□(Roche Diagnostics GmbH) for a nucleic acid amplification instrument. For each gene, 5 µl of BIS-treated DNA solution was added into the PCR reaction mixture which mixed the primer set and the TaqMan probe of concentrations shown in Table 4 into 1×Master_mix, and PCR was carried out in a total volume of 20 µl. PCR amplification was carried out by initial denaturation at 95° C. for 10 min followed by 50 cycles of 95° C. for 10 s, 63° C. for 45 s and 72° C. for 5 s followed by warming of 40° C. for 30 s.

Fluorescent signal was detected after extension reaction at 72° C. of each cycle. Amplification of target gene was monitored by F1/F3 analysis mode in LightCycler software (Roche Diagnostics GmbH), and methylated DNA in 50 µl of BIS-treated DNA solution was quantified using the standard curve which was made with simultaneously measured standards (dilution series of artificially methylated DNA: 1000, 200, 40 and 4 pg/µl). Furthermore, said methylated DNA quantity in solution was multiplied by 50 and was converted to methylated DNA quantity in 1 ml of serum. Said methylated DNA quantity in serum was utilized for statistical analysis and clinical evaluation.

SRD5A2 Gene

Real-time PCR was performed using a self-prepared reagent for an amplification reagent and the LightCycler®2.0 (Roche Diagnostics GmbH) for a nucleic acid amplification instrument. Five µl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 µM dNTPs, 2.5% glycerol and 0.15 unit ZO5 (thermostable DNA polymerase) and PCR was carried out in a total volume of 20 µl PCR amplification was performed by initial denaturation at 95° C. for 2 min followed by 50 cycles of 95° C. for 15 s, 66° C. for 45 s and 72° C. for 5 s followed by warming of 40° C. for 30 s.

Fluorescent signal was detected after extension reaction at 66° C. of each cycle. Amplification of target gene was monitored by F1/F3 analysis mode in LightCycler software (Roche Diagnostics GmbH), and methylated DNA in 50 µl of BIS-treated DNA solution was quantified using the standard curve which was made with simultaneously measured standards (dilution series of artificially methylated DNA: 200, 40, 10 and 4 pg/µl). Furthermore, said methylated DNA quantity in solution was multiplied by 50 and was converted to methylated DNA quantity in 1 ml of serum. Said methylated DNA quantity in serum was utilized for statistical analysis and clinical evaluation.

For the above thirty-one cases of HCV-positive liver cancer patients (patients who were taken a follow-up for over two years after collection of serum and curative resection of liver cancer), the clinical evaluation on detection of a risk of liver cancer was implemented using the data reduction algorithm which has been established during performance evaluation of liver cancer specific methylation genes with a large number of cases (example 3). To be concrete, after logarithmic transformation of methylated DNA quantity of each gene and simultaneously measured DNA amounts in serum followed by calculation of score values by said data reduction algorithm, the difference of said score values between eight cases that developed de novo liver cancer (de novo HCC) within two years after operation (multicentric hepatocarcinogenesis population) and twenty-three cases that developed no metastasis and recurrence in any organs within two years (recurrence-free population) was analyzed with average values by t-test.

As a result, it has been shown that multicentric hepatocarcinogenesis population have significantly lower score values ($p<0.05$) than recurrence-free population by a formula: $-0.042965 \times BASP1$ value$-0.187008 \times SPINT2$ value$-2.600843 \times DNA$ amounts in serum$+9.331859$ in combination with 3 markers of BASP1 gene, SPINT2 gene and DNA amounts in serum (Table 16). Likewise, it has been shown that multicentric hepatocarcinogenesis population have significantly lower score values ($p<0.01$) than recurrence-free population by a formula: $-0.112025 \times SRD5A2$ value$-0.199992 \times SPINT2$ value$-2.696542 \times DNA$ amounts in serum$+9.867470$ in combination with three markers of SRD5A2 gene, SPINT2 gene and DNA amounts in serum (Table 16). There is no significance between the follow-up periods of both populations ($p=0.741$).

Furthermore, when the same thirty-one cases of liver cancer were investigated on a risk of liver cancer divided between cases with score values of 0 and over (twelve cases) and those with score values of below 0 (nineteen cases) that were calculated by a formula: −0.042965×BASP1 value−0.187008×SPINT2 value−2.600843×DNA amounts in serum+9.331859 in combination with three markers of BASP1 gene, SPINT2 gene and DNA amounts in serum, all the twelve cases with score values of 0 and over developed no de novo HCC, but eight (42.1%) of the nineteen cases with score values of below 0 developed de novo HCC (p<0.05 by Fisher's exact test). Furthermore, the exact same result was given by a formula: −0.112025×SRD5A2 value−0.199992×SPINT2 value−2.696542×DNA amounts in serum+9.867470 in combination three markers of SRD5A2 gene, SPINT2 gene and DNA amounts in serum.

Consequently, it has been suggested that measurement of methylated DNA amounts on liver cancer specific methylation genes which have been discovered in this invention, and combination with said measured values and DNA amounts in serum enable us to detect a risk of de novo liver cancer, de novo HCC.

TABLE 16

Clinical evaluation on detection of a risk of liver cancer in combination with liver cancer specific methylation genes and DNA amounts in serum

| Combination | multicentric hepatocarcionogenesis (de novo HCC) | N | Average* | Standard deviation |
|---|---|---|---|---|
| BASP + SPINT + DNA (log transformation) | No | 23 | 0.038832 | 2.0777707 |
| | Yes | 8 | −1.635407 | 1.2643829 |
| | | | Average** | |
| SRD5A + SPINT + DNA (log transformation) | No | 23 | 0.138446 | 1.9552844 |
| | Yes | 8 | −1.641973 | 1.2470458 |

*p < 0.05
**p < 0.01

Example 7

Detection of a Risk of Recurrence of Liver Cancer by Measurement of Liver Cancer Specific Methylation Genes The total DNA was extracted from 1 ml of serum collected from eighty-one cases of HCV-positive liver cancer patients (patients who were taken a follow-up for over one year after collection of serum and curative resection of liver cancer) using the DNA Extractor SP Kit for Serum and Plasma (Wako Pure Chemical Industries, Ltd.) and 50 μl of DNA solution was prepared. Said DNA solution was BIS-treated using a self-prepared. reagent and 50 μl of BIS-treated DNA solution was prepared.

Next, each methylation specific PCR (MSP) for seven liver cancer specific methylation genes (BASP1 gene, SPINT2 gene and SRD5A2 gene) was performed with 5 μl of said BIS-treated DNA solution. In said MSP, by adding TaqMan probe specific to each gene together, quantification of methylated DNA by real-time PCR was carried out. Meanwhile, according to the method described in patent literature 1, the total DNA amount in 1 ml of serum was measured with 1 μl of said BIS-treated DNA solution at the same time. Quantification of methylated DNA was actually performed by the following procedure.

BASP1 Gene and SPINT2 Gene

Real-time PCR was performed using the LightCycler® TaqMan Master Kit (Roche Diagnostics GmbH) for an amplification reagent and the LightCycler® II (Roche Diagnostics GmbH) for a nucleic acid amplification instrument. For each gene, 5 μl of BIS-treated DNA solution was added into the PCR reaction mixture which mixed the primer set and the TaqMan probe of concentrations shown in Table 4 into 1× Master mix, and PCR was carried out in a total volume of 20 μl. PCR amplification was carried out by initial denaturation at 95° C. for 10 min followed by 50 cycles of 95° C. for 10 s, 63° C. for 45 s and 72° C. for 5 s followed by warming of 40° C. for 30 s.

Fluorescent signal was detected after extension reaction at 72° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 1000, 200, 40 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

SRD5A2 Gene

Real-time PCR was performed using a self-prepared reagent for an amplification reagent and the LightCycler®2.0 (Roche Diagnostics GmbH) for a nucleic acid amplification instrument. Five μl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 μM dNTPs, 2.5% glycerol and 0.15 unit ZO5 (thermostable DNA polymerase) and PCR was carried out in a total volume of 20 μl. PCR amplification was performed by initial denaturation at 95° C. for 2 min followed by 50 cycles of 95° C. for 15 s, 66° C. for 45 s and 72° C. for 5 s followed by warming of 40° C. for 30 s.

Fluorescent signal was detected after extension reaction at 66° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 200, 40, 10 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

For the above eighty-one cases of HCV-positive liver cancer patients (patients who were taken a follow-up for over 1 year after collection of serum and curative resection of liver cancer), the clinical evaluation on detection of a risk of recurrence of liver cancer was implemented using the data reduction algorithm which has been established during performance evaluation of liver cancer specific methylation genes with a large number of cases (example 3). To be concrete, after logarithmic transformation of methylated DNA quantity of each gene and simultaneously measured DNA amounts in serum followed by calculation of score values by said data reduction algorithm, the difference of said score values between sixty-eight cases that developed no recurrence within 1 year after operation of liver cancer (liver cancer recurrence-free population) and thirteen cases that developed recurrence within one year (early liver cancer recurrence population) was analyzed with average values by t-test.

As a result, it has been shown that early liver cancer recurrence population have significantly lower score values (p<0.05) than liver cancer recurrence-free population by a formula: −0.042965×BASP1 value−0.187008×SPINT2 value−2.600843×DNA amounts in serum+9.331859 in combination with three markers of BASP1 gene, SPINT2 gene and DNA amounts in serum (Table 17).

Furthermore, when the same eighty-one cases of liver cancer were investigated on a risk of recurrence of liver cancer divided between cases with score values of 0 and over (seventeen cases) and those with score values of below 0 (sixty-four cases) that were calculated by a formula: −0.042965×BASP1 value−0.187008×SPINT2 value−2.600843×DNA amounts in serum+9.331859 in combination with three markers of BASP1 gene, SPINT2 gene and DNA amounts in serum, all the seventeen cases with score values of 0 and over developed no early liver cancer recurrence, but thirteen (20.3%) of the sixty-four cases with score values of below 0 developed early liver cancer recurrence (p=0.06 by Fisher's exact test). Furthermore, the exact same result was given by a formula: −0.112025×SRD5A2 value−0.199992×SPINT2 value−2.696542×DNA amounts in serum+9.867470 in combination with three markers of SRD5A2 gene, SPINT2 gene and DNA amounts in serum.

Consequently, it has been suggested that measurement of methylated DNA amounts on liver cancer specific methylation genes which have been discovered in this invention, and combination with said measured values and DNA amounts in serum enable us to detect a risk of early recurrence of liver cancer.

TABLE 17

Clinical evaluation on detection of a risk of recurrence of liver cancer in combination with liver cancer specific methylation genes and DNA amounts in serum

| Combination | Early recurrence of liver cancer | N | Average* | Standard deviation | Standard error of mean |
|---|---|---|---|---|---|
| BASP + SPINT + DNA (log transformation) | No | 68 | −1.622687 | 2.4766428 | 0.3003370 |
|  | Yes | 13 | −3.806198 | 1.8854879 | 0.5229403 |

*p < 0.005

Example 8

Monitoring of Survival Rate of Liver Cancer with Time by Measurement of Liver Cancer Specific Methylation Genes The total DNA was extracted from 1 ml of serum collected from eighty-seven cases of HCV-positive liver cancer patients (patients who underwent curative resection of liver cancer) using the DNA Extractor SP Kit for Serum and Plasma (Wako Pure Chemical Industries, Ltd.) and 50 μl of DNA solution was prepared. Said DNA solution was BIS-treated using a self-prepared reagent and 50 μl of BIS-treated DNA solution was prepared.

Next, each methylation specific PCR (MSP) for seven liver cancer specific methylation genes (BASP1 gene, SPINT2 gene and SRD5A2 gene) was performed with 5 μl of said BIS-treated DNA solution. In said MSP, by adding TaqMan probe specific to each gene together, quantification of methylated DNA by real-time PCR was carried out. Meanwhile, according to the method described in patent literature 1, the total DNA amount in 1 ml of serum was measured with 1 μl of said BIS-treated DNA solution at the same time. Quantification of methylated DNA was actually performed by the following procedure.

BASP1 Gene and SPINT2 Gene

Real-time PCR was performed using the LightCycler® TaqMan Master Kit (Roche Diagnostics GmbH) for an amplification reagent and the LightCycler® II (Roche Diagnostics GmbH) for a nucleic acid amplification instrument. For each gene, 5 pl of BIS-treated DNA solution was added into the PCR reaction mixture which mixed the primer set and the TaqMan probe of concentrations shown in Table 4 into 1× Master mix, and PCR was carried out in a total volume of 20 μl. PCR amplification was carried out by initial denaturation at 95° C. for 10 min followed by 50 cycles of 95° C. for 10 s, 63° C. for 45 s and 72° C. for 5 s followed by warming of 40° C. for 30 s.

Fluorescent signal was detected after extension reaction at 72° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 1000, 200, 40 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

SRD5A2 Gene

Real-time PCR was performed using a self-prepared reagent for an amplification reagent and the LightCycler®2.0 (Roche Diagnostics GmbH) for a nucleic acid amplification instrument. Five μl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 μM dNTPs, 2.5% glycerol and 0.15 unit ZO5 (thermostable DNA polymerase) and PCR was carried out in a total volume of 20 μl. PCR amplification was performed by initial denaturation at 95° C. for 2 min followed by 50 cycles of 95° C. for 15 s, 66° C. for 45 s and 72° C. for 5 s followed by warming of 40° C. for 30 s.

Fluorescent signal was detected after extension reaction at 66° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 200, 40, 10 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

For the above eighty-seven cases of HCV-positive liver cancer patients (patients who underwent curative resection of liver cancer), the clinical evaluation on monitoring of survival rate of liver cancer with time was implemented using the data reduction algorithm which has been established during performance evaluation of liver cancer specific methylation genes with a large number of cases (example 3). To be concrete, after logarithmic transformation of methylated DNA quantity of each gene and simultaneously measured DNA amounts in serum followed by calculation of score values by said data reduction algorithm, the survival rate with time after operation of liver cancer was compared between cases with score values of 0 and over (twenty-two cases) and those with score values of below 0 (sixty-five cases).

As a result, as shown in FIG. 5, being calculated by a formula: −0.042965×BASP1 value−0.187008×SPINT2 value−2.600843×DNA amounts in serum+9.331859 in combination with three markers of BASP1 gene, SPINT2 gene and DNA amounts in serum, twenty-two cases with score values of 0 and over had significantly higher survival rate than sixty-five cases with score values of below 0 (Overall survival rate: p=0.0289, Disease-free survival rate: p=0.0372).

Overall survival rate says a method to express the survival rate during follow-up period for patients regardless of the cause of death including recurrence of liver caner (patients who died of other diseases, aging, burst of esophageal varices from liver cirrhosis but not liver cancer, other cancers, traffic accident or suicide, will be included.). Disease-free survival rate (recurrence-free survival rate) says a method to express whether metastasis or recurrence of liver cancer have been observed or not during follow-up period in surviving patients.

Overall survival rate: Percentage of surviving patients at some day (point) after operation.

Disease-free survival rate: Percentage of patients without metastasis or recurrence of liver cancer at some day (point) in surviving patients.

Consequently, it has been suggested that measurement of methylated DNA amounts on liver cancer specific methylation genes which have been discovered in this invention, and combination with said measured values and DNA amounts in serum is useful for monitoring of survival rate with time after operation of liver cancer.

Example 9

Detection of Progression of Liver Cancer by Measurement of Liver Cancer Specific Methylation Genes The total DNA was extracted from 1 ml of serum collected from one hundred and forty-nine cases of HCV-positive liver cancer patients using the DNA Extractor SP Kit for Serum and Plasma (Wako Pure Chemical Industries, Ltd.) and 50 μl of DNA solution was prepared. Said DNA solution was BIS-treated using a self-prepared reagent and 50 μl of BIS-treated DNA solution was prepared.

Next, each methylation specific PCR (MSP) for seven liver cancer specific methylation genes (BASP1 gene, SPINT2 gene and SRD5A2 gene) was performed with 5 μl of said BIS-treated DNA solution. In said MSP, by adding TaqMan probe specific to each gene together, quantification of methylated DNA by real-time PCR was carried out. Meanwhile, according to the method described in patent literature 1, the total DNA amount in 1 ml of serum was measured with 1 μl of said BIS-treated DNA solution at the same time. Quantification of methylated DNA was actually performed by the following procedure.

BASP1 Gene and SPINT2 Gene

Real-time PCR was performed using the LightCycler® TaqMan Master Kit (Roche Diagnostics GmbH) for an amplification reagent and the LightCycler®□(Roche Diagnostics GmbH) for a nucleic acid amplification instrument. For each gene, 5 μl of BIS-treated DNA solution was added into the PCR reaction mixture which mixed the primer set and the TaqMan probe of concentrations shown in Table 4 into 1× Master mix, and PCR was carried out in a total volume of 20 μl. PCR amplification was carried out by initial denaturation at 95° C. for 10 min followed by 50 cycles of 95° C. for 10 s, 63° C. for 45 s and 72° C. for 5 s followed by warming of 40° C. for 30 s.

Fluorescent signal was detected after extension reaction at 72° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 1000, 200, 40 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

SRD5A2 Gene

Real-time PCR was performed using a self-prepared reagent for an amplification reagent and the LightCycler®2.0 (Roche Diagnostics GmbH) for a nucleic acid amplification instrument. Five μl of BIS-treated DNA solution was added after mixing the primer set, the TaqMan probe, potassium acetate (pH7.5) and Aptamer48 of concentrations or amounts shown in Table 5 into the PCR reaction mixture which composed of 50 mM Tricine (pH8.3), 3 mM magnesium acetate, 375 μM dNTPs, 2.5% glycerol and 0.15 unit ZO5 (thermostable DNA polymerase) and PCR was carried out in a total volume of 20 μl. PCR amplification was performed by initial denaturation at 95° C. for 2 min followed by 50 cycles of 95° C. for 15 s, 66° C. for 45 s and 72° C. for 5 s followed by war 40° C. for 30 s.

Fluorescent signal was detected after extension reaction at 66° C. of each cycle. Amplification of target gene was monitored by F1/F3 analysis mode in LightCycler software (Roche Diagnostics GmbH), and methylated DNA in 50 μl of BIS-treated DNA solution was quantified using the standard curve which was made with simultaneously measured standards (dilution series of artificially methylated DNA: 200, 40, 10 and 4 pg/μl). Furthermore, said methylated DNA quantity in solution was multiplied by 50 and was converted to methylated DNA quantity in 1 ml of serum. Said methylated DNA quantity in serum was utilized for statistical analysis and clinical evaluation.

For the above one hundred and forty-nine cases of HCV-positive liver cancer patients, the clinical evaluation on detection of progression of liver cancer was implemented using three liver cancer specific methylation genes, DNA amounts in serum and the data reduction algorithm which has been established during performance evaluation of liver cancer specific methylation genes with a large number of cases (example 3). To be concrete, correlation between tumor size, and methylated DNA quantity, DNA amounts in serum or score values calculated by said data reduction algorithm after logarithmic transformation of methylated DNA quantity and DNA amounts in serum, was evaluated with Pearson's correlation coefficient test.

As a result, methylated DNA quantity of BASP1 gene tended to be positively correlated with tumor size (r=0.216, p<0.01) (Table 18). Furthermore, score values that were calculated by a formula: −0.042965×BASP1 value−0.187008×SPINT2 value−2.600843×DNA amounts in serum+9.331859 in combination with three markers of BASP1 gene, SPINT2 gene and DNA amounts in serum or by a formula: −0.112025×SRD5A2 value−0.199992×SPINT2 value−2.696542×DNA amounts in serum+9.867470 in combination with three markers of SRD5A2 gene, SPINT2 gene and DNA amounts in serum, tended to be negatively correlated with tumor size (r=−0.235, p<0.005, r=−0.244, p<0.005) (Table 18).

Consequently, it has been suggested that measurement of methylated DNA amounts on liver cancer specific methylation genes which have been discovered in this invention, or combination with said measured values and DNA amounts in serum are useful for detection of tumor size of liver cancer, progression of liver cancer.

TABLE 18

Clinical evaluation on detection of progression of liver cancer with methylated DNA quantity of liver cancer specific methylation gene, or in combination with liver cancer specific methylation genes and DNA amounts in serum

| N = 149 | | Tumor size | DNA amount in serum | BASP1 | SPINT2 | SRD5A2 | BASP + SPINT + DNA (log transformation) | SRD5A + SPINT + DNA (log transformation) |
|---|---|---|---|---|---|---|---|---|
| Tumor size | Pearson coefficient of correlation | 1.000 | 0.121 | 0.216 | −0.028 | −0.036 | −0.235 | −0.244 |
| | Probability (two-sided) | — | 0 | 0.008 | 0.736 | 0.660 | 0.004 | 0.003 |

INDUSTRIAL APPLICABILITY

This invention is used for testing and diagnosis of liver cancer, especially screening tests of liver cancer, detection of a precancerous lesion, detection of a risk of recurrence after treatment of liver cancer, detection of malignancy of liver cancer and monitoring of progression of liver cancer with time, and can be utilized in clinical diagnostic, pharmaceutical, reagent and medical instrument industries.

SEQUENCE LISTING

Figure 1:
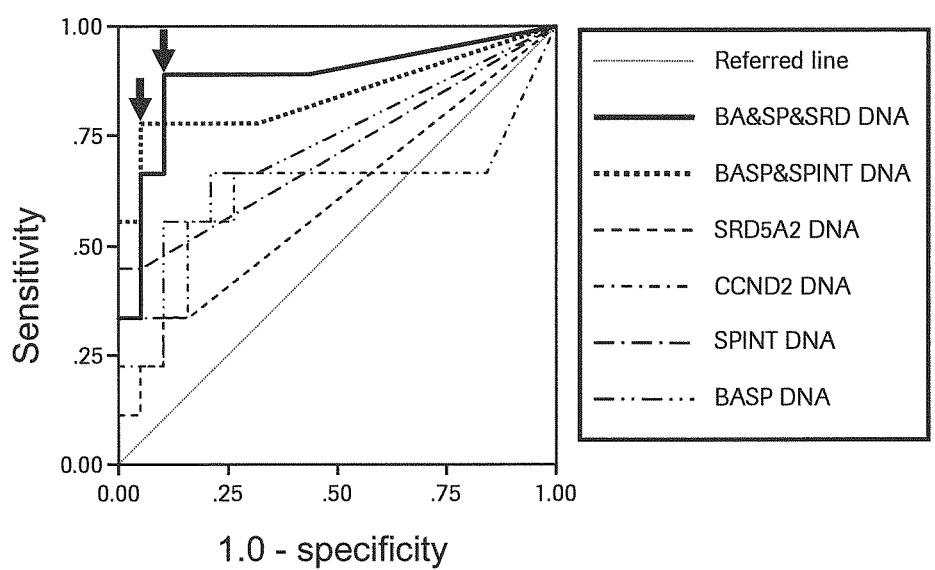
FIG. 1. Results of performance evaluation of liver cancer specific methylation genes by ROC analysis FIG. 2. Results of performance evaluation of liver cancer specific methylation genes by FLC analysis and ROC analysis: Ability to detect liver cancer (BASP1+SPINT2+CFTR, sensitivity: 70%, specificity: 80%, recognition rate: 74%)
Figure 2:
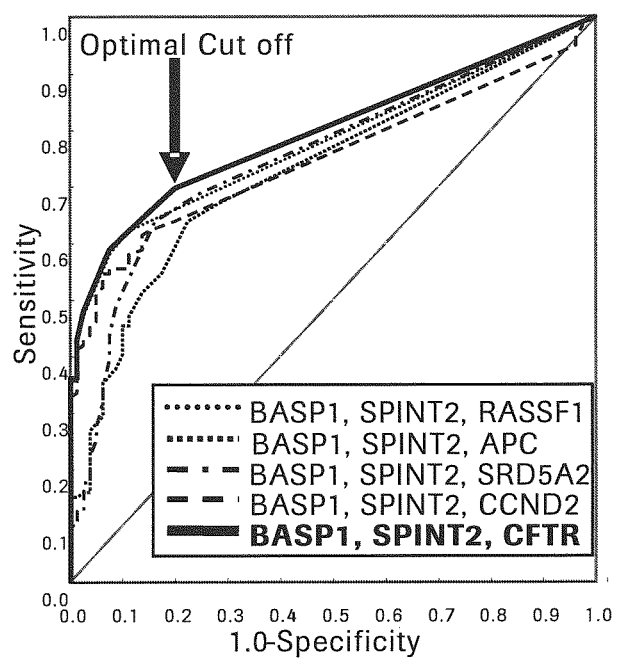
Figure 3:
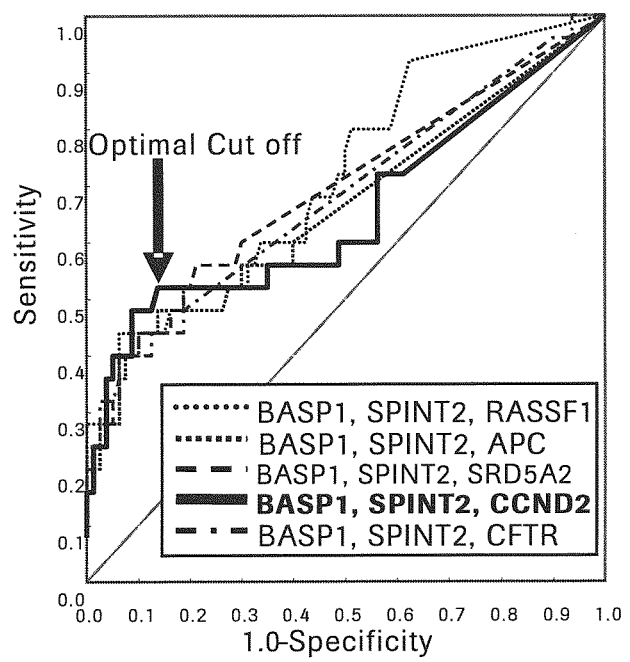
FIG. 3. Results of performance evaluation of liver cancer (liver cancer in early stage: Stage I and below 3 cm) specific methylation genes by FLC analysis and ROC analysis: Ability to detect liver cancer in early stage (BASP1+SPINT2+CCND2, sensitivity: 52%, specificity: 86%, recognition rate: 78%)
Figure 4:
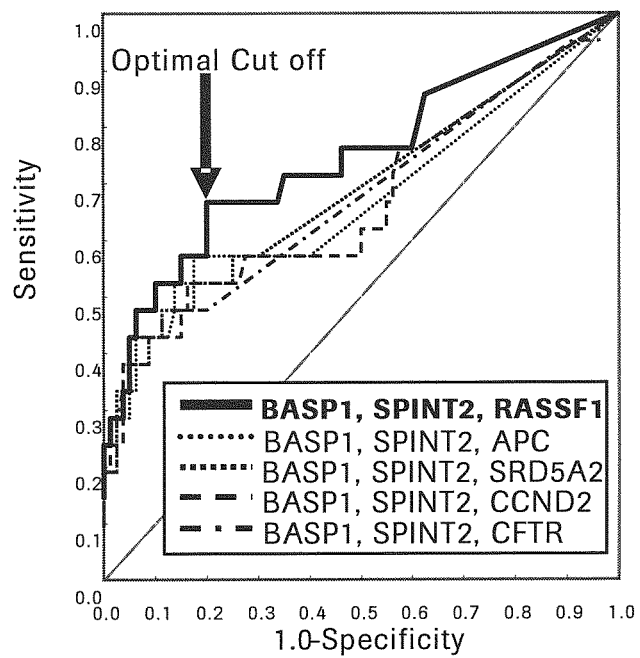
FIG. 4. Results of performance evaluation of liver cancer (liver cancer in early stage: Well-differentiated) specific methylation genes by FLC analysis and ROC analysis: Ability to detect liver cancer in early stage (BASP1+SPINT2+RASSF1, sensitivity: 67%, specificity: 80%, recognition rate: 77%)
Figure 5:
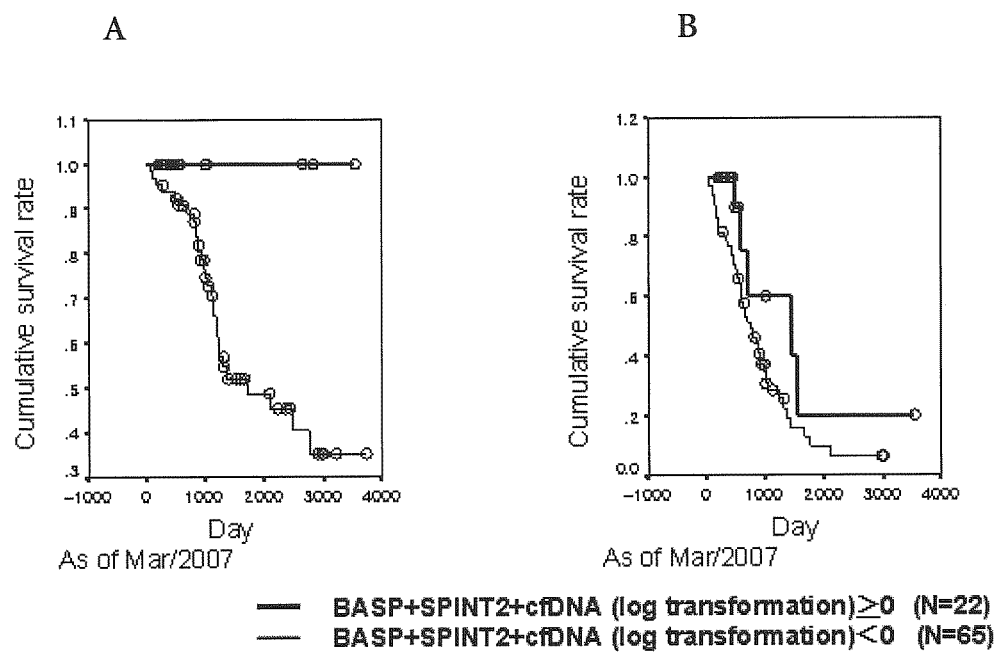
FIG. 5. Results of clinical evaluation on association between measured values of liver cancer specific methylation genes and DNA amounts in serum, and survival rate (Overall survival rate and disease-free survival rate) after operation of liver cancer; A: Overall survival, P=0.0289 by log rank test; B: Disease free survival, P=0.0372 by log rank test While the invention has been described in detail with reference to specific examples, it will be apparent to one skilled in the art that various modifications can be made within the scope of this invention. Thus the scope of the invention should not be limited by the examples described herein, but by the claims presented below.

```
<160> NUMBER OF SEQ ID NOS: 39

<210> SEQ ID NO 1
<211> LENGTH: 22
<212> TYPE: DNA
<213> ORGANISM: Artificial Sequence
<220> FEATURE:
<223> OTHER INFORMATION: BASP1_MSF primer

<400> SEQUENCE: 1
tgttcgtttt tttagggtat tc                                           22

<210> SEQ ID NO 2
<211> LENGTH: 19
<212> TYPE: DNA
<213> ORGANISM: Artificial Sequence
<220> FEATURE:
<223> OTHER INFORMATION: BASP1_MSR primer

<400> SEQUENCE: 2
aattaaccga aacaacccg                                                19

<210> SEQ ID NO 3
<211> LENGTH: 19
<212> TYPE: DNA
<213> ORGANISM: Artificial Sequence
<220> FEATURE:
<223> OTHER INFORMATION: SPINT2_MSF primer

<400> SEQUENCE: 3
```

```
tcggttatttt tcgggagtc                                          19

<210> SEQ ID NO 4
<211> LENGTH: 19
<212> TYPE: DNA
<213> ORGANISM: Artificial Sequence
<220> FEATURE:
<223> OTHER INFORMATION: SPINT2_MSR primer

<400> SEQUENCE: 4
cgcctacgac actcaacga                                           19

<210> SEQ ID NO 5
<211> LENGTH: 17
<212> TYPE: DNA
<213> ORGANISM: Artificial Sequence
<220> FEATURE:
<223> OTHER INFORMATION: APC_MSF primer

<400> SEQUENCE: 5
agtgcgggtc gggaagc                                             17

<210> SEQ ID NO 6
<211> LENGTH: 22
<212> TYPE: DNA
<213> ORGANISM: Artificial Sequence
<220> FEATURE:
<223> OTHER INFORMATION: APC_MSR primer

<400> SEQUENCE: 6
aaccacatat cgatcacgta cg                                       22

<210> SEQ ID NO 7
<211> LENGTH: 27
<212> TYPE: DNA
<213> ORGANISM: Artificial Sequence
<220> FEATURE:
<223> OTHER INFORMATION: CCND2_MSF primer

<400> SEQUENCE: 7
tttgatttaa gtatgcgtta gagtacg                                  27

<210> SEQ ID NO 8
<211> LENGTH: 25
<212> TYPE: DNA
<213> ORGANISM: Artificial Sequence
<220> FEATURE:
<223> OTHER INFORMATION: CCND2_MSR primer

<400> SEQUENCE: 8
actttctccc taaaaaccga ctacg                                    25

<210> SEQ ID NO 9
<211> LENGTH: 19
<212> TYPE: DNA
<213> ORGANISM: Artificial Sequence
<220> FEATURE:
<223> OTHER INFORMATION: CFTR_MSF primer

<400> SEQUENCE: 9
aatcgggaaa gggaggtgc                                           19

<210> SEQ ID NO 10
<211> LENGTH: 20
<212> TYPE: DNA
```

```
<213> ORGANISM: Artificial Sequence
<220> FEATURE:
<223> OTHER INFORMATION: CFTR_MSR primer

<400> SEQUENCE: 10
accgaatact acctaatccg                                              20

<210> SEQ ID NO 11
<211> LENGTH: 18
<212> TYPE: DNA
<213> ORGANISM: Artificial Sequence
<220> FEATURE:
<223> OTHER INFORMATION: RASSF1_MSF primer

<400> SEQUENCE: 11
gcgttgaagt cggggttc                                                18

<210> SEQ ID NO 12
<211> LENGTH: 24
<212> TYPE: DNA
<213> ORGANISM: Artificial Sequence
<220> FEATURE:
<223> OTHER INFORMATION: RASSF1_MSR primer

<400> SEQUENCE: 12
cccgtacttc gctaacttta aacg                                         24

<210> SEQ ID NO 13
<211> LENGTH: 21
<212> TYPE: DNA
<213> ORGANISM: Artificial Sequence
<220> FEATURE:
<223> OTHER INFORMATION: SRD5A2_MSF primer

<400> SEQUENCE: 13
aatcgcgtta gggttggacg c                                            21

<210> SEQ ID NO 14
<211> LENGTH: 18
<212> TYPE: DNA
<213> ORGANISM: Artificial Sequence
<220> FEATURE:
<223> OTHER INFORMATION: SRD5A2_MSR primer

<400> SEQUENCE: 14
aacgccaaac gccacccg                                                18

<210> SEQ ID NO 15
<211> LENGTH: 25
<212> TYPE: DNA
<213> ORGANISM: Artificial Sequence
<220> FEATURE:
<223> OTHER INFORMATION: BASP1_F primer

<400> SEQUENCE: 15
tttgttaata ggtaagtaaa gtgaa                                        25

<210> SEQ ID NO 16
<211> LENGTH: 24
<212> TYPE: DNA
<213> ORGANISM: Artificial Sequence
<220> FEATURE:
<223> OTHER INFORMATION: BASP1_R primer

<400> SEQUENCE: 16
ttaaaataaa ccccaactac aaac                                         24
```

<210> SEQ ID NO 17
<211> LENGTH: 21
<212> TYPE: DNA
<213> ORGANISM: Artificial Sequence
<220> FEATURE:
<223> OTHER INFORMATION: SPINT2_F primer

<400> SEQUENCE: 17
ggaagggtgg taggtgttta g                                              21

<210> SEQ ID NO 18
<211> LENGTH: 22
<212> TYPE: DNA
<213> ORGANISM: Artificial Sequence
<220> FEATURE:
<223> OTHER INFORMATION: SPINT2_R primer

<400> SEQUENCE: 18
tacctaaatc tactcctcac tc                                             22

<210> SEQ ID NO 19
<211> LENGTH: 21
<212> TYPE: DNA
<213> ORGANISM: Artificial Sequence
<220> FEATURE:
<223> OTHER INFORMATION: APC_F primer

<400> SEQUENCE: 19
ttgtttgttg gggattgggg t                                              21

<210> SEQ ID NO 20
<211> LENGTH: 24
<212> TYPE: DNA
<213> ORGANISM: Artificial Sequence
<220> FEATURE:
<223> OTHER INFORMATION: APC_R primer

<400> SEQUENCE: 20
tacaaaaaat ccatctccaa tact                                           24

<210> SEQ ID NO 21
<211> LENGTH: 25
<212> TYPE: DNA
<213> ORGANISM: Artificial Sequence
<220> FEATURE:
<223> OTHER INFORMATION: CCND2_F primer

<400> SEQUENCE: 21
tttttggagt gaaatatatt aaagg                                          25

<210> SEQ ID NO 22
<211> LENGTH: 22
<212> TYPE: DNA
<213> ORGANISM: Artificial Sequence
<220> FEATURE:
<223> OTHER INFORMATION: CCND2_R primer

<400> SEQUENCE: 22
cccctacatc tactaacaaa cc                                             22

<210> SEQ ID NO 23
<211> LENGTH: 20
<212> TYPE: DNA
<213> ORGANISM: Artificial Sequence
<220> FEATURE:

```
<223> OTHER INFORMATION: CFTR_F primer

<400> SEQUENCE: 23
gaggaggagg aaggtaggtt                                              20

<210> SEQ ID NO 24
<211> LENGTH: 21
<212> TYPE: DNA
<213> ORGANISM: Artificial Sequence
<220> FEATURE:
<223> OTHER INFORMATION: CFTR_R primer

<400> SEQUENCE: 24
ccacccctcc cttttactct t                                            21

<210> SEQ ID NO 25
<211> LENGTH: 21
<212> TYPE: DNA
<213> ORGANISM: Artificial Sequence
<220> FEATURE:
<223> OTHER INFORMATION: RASSF1_F primer

<400> SEQUENCE: 25
tagtttggat tttgggggag g                                            21

<210> SEQ ID NO 26
<211> LENGTH: 21
<212> TYPE: DNA
<213> ORGANISM: Artificial Sequence
<220> FEATURE:
<223> OTHER INFORMATION: RASSF1_R primer

<400> SEQUENCE: 26 ctaccccttta actaccccttt c                                          21

<210> SEQ ID NO 27
<211> LENGTH: 24
<212> TYPE: DNA
<213> ORGANISM: Artificial Sequence
<220> FEATURE:
<223> OTHER INFORMATION: SRD5A2_F primer

<400> SEQUENCE: 27
taagttatgg aaggatagtt taag                                         24

<210> SEQ ID NO 28
<211> LENGTH: 23
<212> TYPE: DNA
<213> ORGANISM: Artificial Sequence
<220> FEATURE:
<223> OTHER INFORMATION: SRD5A2_R primer

<400> SEQUENCE: 28
aacaactcct acaaaaacca aac                                          23

<210> SEQ ID NO 29
<211> LENGTH: 22
<212> TYPE: DNA
<213> ORGANISM: Artificial Sequence
<220> FEATURE:
<223> OTHER INFORMATION: SPINT2_HMF primer

<400> SEQUENCE: 29
gttttttgtt tgttyggtta tt                                           22
```

```
<210> SEQ ID NO 30
<211> LENGTH: 20
<212> TYPE: DNA
<213> ORGANISM: Artificial Sequence
<220> FEATURE:
<223> OTHER INFORMATION: SPINT2_HMR primer

<400> SEQUENCE: 30
acctaaatct actcctcact                                              20

<210> SEQ ID NO 31
<211> LENGTH: 25
<212> TYPE: DNA
<213> ORGANISM: Artificial Sequence
<220> FEATURE:
<223> OTHER INFORMATION: BASP1_TMP probe

<400> SEQUENCE: 31
acgctactac ttacgaacgc tcgaa                                        25

<210> SEQ ID NO 32
<211> LENGTH: 23
<212> TYPE: DNA
<213> ORGANISM: Artificial Sequence
<220> FEATURE:
<223> OTHER INFORMATION: SPINT2_TMP probe

<400> SEQUENCE: 32
ccaacgcgcg aaaatcgcca aaa                                          23

<210> SEQ ID NO 33
<211> LENGTH: 25
<212> TYPE: DNA
<213> ORGANISM: artificial sequence
<220> FEATURE:
<223> OTHER INFORMATION: APC_TMP probe

<400> SEQUENCE: 33
aaaacgccct aatccgcatc caacg                                        25

<210> SEQ ID NO 34
<211> LENGTH: 26
<212> TYPE: DNA
<213> ORGANISM: Artificial Sequence
<220> FEATURE:
<223> OTHER INFORMATION: CCND2_TMP probe

<400> SEQUENCE: 34
aatcgccgcc aacacgatcg acccta                                       26

<210> SEQ ID NO 35
<211> LENGTH: 21
<212> TYPE: DNA
<213> ORGANISM: Artificial Sequence
<220> FEATURE:
<223> OTHER INFORMATION: CFTR_TMP probe

<400> SEQUENCE: 35
tccacccact acgcaccccc g                                            21

<210> SEQ ID NO 36
<211> LENGTH: 24
<212> TYPE: DNA
<213> ORGANISM: Artificial Sequence
<220> FEATURE:
<223> OTHER INFORMATION: RASSF1_TMP probe
```

```
<400> SEQUENCE: 36
acaaacgcga accgaacgaa acca                                          24

<210> SEQ ID NO 37
<211> LENGTH: 22
<212> TYPE: DNA
<213> ORGANISM: Artificial Sequence
<220> FEATURE:
<223> OTHER INFORMATION: SRD5A2_TMP probe

<400> SEQUENCE: 37
ctcgacctta actcccgccc ct                                            22

<210> SEQ ID NO 38
<211> LENGTH: 22
<212> TYPE: DNA
<213> ORGANISM: Artificial Sequence
<220> FEATURE:
<223> OTHER INFORMATION: SPINT2_HMBF probe

<400> SEQUENCE: 38
ttggttattt ttgggagttg tt                                            22

<210> SEQ ID NO 39
<211> LENGTH: 21
<212> TYPE: DNA
<213> ORGANISM: Artificial Sequence
<220> FEATURE:
<223> OTHER INFORMATION: SPINT2_HMBR probe

<400> SEQUENCE: 39
tcctcactca caccctcacc a                                             21
```

The invention claimed is:

1. A method for detecting the presence or amount of methylated cytosine specific to liver cancer on a region containing CpG sequences in BASP1 gene and SRD5A2 gene comprising the following steps of (a) to (d):
   (a) isolating genomic DNA from a patient sample;
   (b) contacting the DNA with a reagent for chemical or enzymatic treatment of the DNA in order to discriminate between methylated and unmethylated cytosines;
   (c) amplifying methylated cytosine-containing regions of BASP1 gene and SRD5A2 gene present in the genomic DNA using PCR utilizing at least one of SEQ ID NOs: 1, 2, 13, 14, 15, 16, 27, 28, 31 and 37; and
   (d) determining the presence or amount of methylated cytosine in BASP1 gene and SRD5A2 gene,
   wherein the presence or amount of methylated cytosine is an indication that said patient is afflicted with liver cancer, has an increased risk of occurrence or recurrence after treatment of liver cancer or has a progression of liver cancer with time.

2. The method according to claim 1, wherein amplifying in step (c) is performed in the presence of at least one PCR primer complementary to at least one of said cytosine-containing regions that specifically hybridizes to said cytosine-containing regions when said cytosines are methylated.

3. The method according to claim 1, wherein amplifying in step (c) is performed in the presence of blocker oligonucleotides which partially overlap with amplification primers and are complementary to at least one of said cytosine-containing regions and specifically hybridize to said regions when the cytosines are not methylated.

4. The method according to claim 1, wherein amplifying in step (c) is performed by real-time PCR with a fluorescent probe.

5. The method according to claim 1, wherein determination of the presence or amount of methylated cytosine in step (d) is performed by sequencing or by mass spectrometry.

6. The method according to claim 1, wherein chemical treatment in step (b) consists of conversion of unmethylated cytosine to uracil.

7. The method according to claim 1, wherein the chemical reagent in step (b) is a bisulfite-containing reagent.

8. The method according to claim 7, wherein the bisulfite-containing reagent comprises sodium bisulfate or sodium sulfite or 6-hydroxy-2,5,7,8-tetramethylchroman-2-carboxylic acid.

9. The method according to claim 1, wherein enzymatic treatment in step (b) is carried out with a methylation-sensitive restriction enzyme.

10. The method according to claim 1, further comprising step (e) wherein protein concentration or free floating DNA amounts of one or more genes selected from SPINT2, APC, CCND2, CFTR and RASSF1 are further determined in the sample.

11. The method according to claim 10, further comprising determining protein concentration or free floating DNA amounts of one or more genes selected from GSTP1, AFP and PWKA-II.

12. The method according to claim 1, wherein liver cancer is in early stage.

13. The method according claim 1, wherein the sample is derived from human sera, plasma, whole blood, tissues, blood cells, excretions or secretions.

14. The method of claim 1, wherein amplifying methylated cytosine-containing regions of BASP1 gene is performed utilizing SEQ ID NOs: 1, 2 and 31 or 15, 16 and 31, and amplifying methylated cytosine-containing regions of SRD5A2 gene is performed utilizing SEQ ID NOs: 13, 14 and 37 or 27, 28 and 37.

* * * * *